United States Patent
van den Bosch et al.

(10) Patent No.: US 12,371,704 B2
(45) Date of Patent: *Jul. 29, 2025

(54) BRASSICA OLERACEA PLANTS WITH IMPROVED NUTRITIONAL VALUE

(71) Applicants: Seminis Vegetable Seeds, Inc., St. Louis, MO (US); PLANT BIOSCIENCE LIMITED, Norwich (GB)

(72) Inventors: Franciscus G. van den Bosch, Kesteren (NL); Gerard N. Koorevaar, Ede (NL); Richard F. Mithen, Norwich (GB)

(73) Assignees: Seminis Vegetable Seeds, Inc., St. Louis, MO (US); PLANT BIOSCIENCE LIMITED, Norwich (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/405,535

(22) Filed: Jan. 5, 2024

(65) Prior Publication Data
US 2024/0229057 A1 Jul. 11, 2024

Related U.S. Application Data

(60) Division of application No. 17/175,280, filed on Feb. 12, 2021, now Pat. No. 11,898,150, which is a continuation of application No. 16/431,310, filed on Jun. 4, 2019, now Pat. No. 10,982,220, which is a division of application No. 15/359,429, filed on Nov. 22, 2016, now Pat. No. 10,385,353, which is a continuation of application No. 14/025,512, filed on Sep. 12, 2013, now Pat. No. 9,617,554.

(60) Provisional application No. 61/700,762, filed on Sep. 13, 2012.

(51) Int. Cl.
C12N 15/82 (2006.01)
A01H 1/02 (2006.01)
A01H 1/04 (2006.01)
A01H 5/02 (2018.01)
A01H 5/10 (2018.01)
C12Q 1/68 (2018.01)
C12Q 1/6895 (2018.01)

(52) U.S. Cl.
CPC ........... *C12N 15/8246* (2013.01); *A01H 1/02* (2013.01); *A01H 1/04* (2013.01); *A01H 5/02* (2013.01); *A01H 5/10* (2013.01); *C12Q 1/6895* (2013.01); *C12Q 2600/13* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 5,492,547 | A | 2/1996 | Johnson |
| 6,340,784 | B1 | 1/2002 | Mithen |
| 6,361,812 | B1 | 3/2002 | Ekanayake |
| 8,492,616 | B2 | 7/2013 | Mero |
| 9,096,863 | B2 | 8/2015 | Geu-Flores et al. |
| 9,248,474 | B2 | 2/2016 | Teramoto et al. |
| 9,567,650 | B2 | 2/2017 | Mithen et al. |
| 9,617,554 | B2 * | 4/2017 | van den Bosch ........ A01H 5/02 |
| 10,385,353 | B2 * | 8/2019 | van den Bosch .. C12N 15/8246 |
| 10,472,685 | B2 | 11/2019 | Mithen et al. |
| 10,982,220 | B2 * | 4/2021 | van den Bosch .. C12N 15/8246 |
| 11,685,959 | B2 | 6/2023 | Mithen et al. |
| 11,898,150 | B2 * | 2/2024 | van den Bosch ........ A01H 5/02 |
| 2010/0011462 | A1 | 1/2010 | Kliebenstein et al. |
| 2017/0137897 | A1 | 5/2017 | Mithen et al. |
| 2020/0172986 | A1 | 6/2020 | Mithen et al. |
| 2023/0366039 | A1 | 11/2023 | Mithen et al. |

FOREIGN PATENT DOCUMENTS

| | | |
|---|---|---|
| EP | 1069819 | 7/2002 |
| JP | 2011-97921 | 5/2011 |
| WO | 99/52345 A1 | 10/1999 |
| WO | 2004089065 | 10/2004 |
| WO | 2010/001119 | 1/2010 |
| WO | 2011/158759 | 12/2011 |

OTHER PUBLICATIONS

Zang et al (The FEBS Journal 276:3559-3574 (Year: 2009).*
U.S. Appl. No. 18/309,398, filed Apr. 28, 2023, Mithen et al.
"Apio, Inc. is proud to introduce Eat Smart® Beneforte® broccoli," http://www.eatsmartbeneforte.com, downloaded Dec. 19, 2014.
About Beneforte, Beneforte Super Broccoli, IFR Institute of Food Research, pp. 1-3; downloaded Nov. 9, 2015.
Associate website for Beneforte broccoli, <http://www.benforte.com/>, dated Aug. 2, 2011.

(Continued)

Primary Examiner — Brent T Page
(74) Attorney, Agent, or Firm — Dentons US LLP

(57) ABSTRACT

The invention provides compositions and methods relating to the elevation of glucoraphanin compared to standard *Brassica oleracea* varieties. The invention also relates to the production of hybrid varieties having desired glucosinolate contents. The invention further provides plants, plant parts, and seeds comprising such traits and comprising a Myb28 allele from *Brassica villosa* that is not genetically linked to an ELONG allele from *Brassica villosa*.

3 Claims, 7 Drawing Sheets
Specification includes a Sequence Listing.

(56) References Cited

OTHER PUBLICATIONS

Better Broccoli, Produce Processing (brochure), pp. 1-3, published Dec. 16, 2010.
Super-broccoli a 'fantastic achievement,' http://www.smh.com.au/lifestyle/diet-and-fitness/superbrocolli-a-fantastic-achievement-20111005-118i2.html, dated Oct. 5, 2011.
'Superbroccoli' goes on sale in UK, http://www.telegraph.co.uk/foodanddrink/8804965/Superbroccoli-goes-on-sale-in UK.html, dated Oct. 4, 2011.
Augustine et al., "Four genes encoding MYB28, a major transcriptional regulator of the aliphatic glucosinolate pathway, are differentially expressed in the allopolyploid *Brassica juncea*," Journal of Experimental Botany 64:4907-4921, 2013.
Batley et al., "SNP Application in Plants," Association Mapping in Plants. Chapter 6, pp. 95-102, 2007.
Bellostas et al., "Glucosinolate profiling of seeds and sprouts of *B. oleracea* varieties used for food," Scientia Horticulturae 114:234-242, 2007.
Bisht et al., "Fine mapping of loci involved with glucosinolate biosynthesis in oilseed mustard (*Brassica juncea*) using genomic information from allied species," Theor. Appl. Genet., 118(3):413-421, 2009.
Bouhoun et al., "Alignment of the conserved C genomes of *Brassica oleracea* and *Brassica napus*," Theor. Appl. Genet.; 93:833-839, 1996.
Cheng et al., "Research Progress on Regulation and Synthesis Genes on Glucosinolates Biosynthesis in Crucifer," China Vegetables 12:1-6, 2010.
Cheng et al., "BRAD, the genetics and genomics database for *Brassica* plants," BMC Plant Biology 11:136, 2011.
Crowhurst, "Dutch seed Open Days—Widening the field", http://hortweek.com/Edibles/article/1099235/dutch-seed-opendays-widening-field; pp. 1-5; Oct. 21, 2011.
EBI Accession No. ARA20191, "Thale cress Myb29 amplifying PCR primer, MYB29 f.," May 1, 2008.
EBI Accession No. HD429246, "Sequence 305962 from Patent EP2213738," Aug. 18, 2010.
GenBank Accession No. AB671773, dated Apr. 20, 2012.
GenBank Accession No. AC232495, dated Sep. 11, 2008.
GenBank Accession No. CP002688.1, dated Jun. 16, 2011.
GenBank Accession No. FJ584288, dated Aug. 12, 2009.
GenBank Accession No. FJ584289, dated Aug. 12, 2009.
GenBank Accession No. GQ478992, dated Apr. 4, 2011.
GenBank Accession No. HQ270468, dated Nov. 29, 2010.
Gigolashvili et al., "The R2R3-MYB transcription factor HAG1/MYB28 is a regulator of methionine-derived glucosinolate biosynthesis in *Arabidopsis thaliana*," The Plant Journal 51(2):247-261, 2007.
Harper et al., "Associative transcriptomics of traits in the polyploid crop species *Brassica napus*," Nature Biotechnology 30(8):798-802, 2012.
Hirani, "Qtl Mapping, Gene Identification and Genetic Manipulation of Glucosinolates in *Brassica rapa* L.," PhD Thesis, University of Manitoba, pp. 1-164, 2011.
Hsu et al., "Generation of Se-fortified broccoli as functional food: impact of Se fertilization on S metabolism," Plant, Cell & Environment 34:192-207, 2011.
Joseph et al., "Genetic Variation in the Nuclear and Organellar Genomes Modulates Stochastic Variation in the Metabolome, Growth, and Defense," PloS Genet 11(1); e1004779. Doi:10.137/journal.pqen. 1004779; 2015.
Kliebenstein et al., "Comparative Quantitative Trait Loci Mapping of Aliphatic, Indolic and Benzylic Glucosinolate Production in *Arabidopsis thaliana* Leaves and Seeds," Genetics 159:359-370, 2001.
Lander et al., "MAPMAKER: an interactive computer package for constructing primary genetic linkage maps of experimental and natural populations," Genomics 1(2):174-181, 1987.
Lander et al.,"Mapping mendelian factors underlying quantitative traits using RFLP linkage maps," Genetics 121 (1):185-199, 1989.
Lou et al., "Quantitative trait loci for glucosinolate accumulation in *Brassica rapa* leaves," New Phytologist 179 (4):1017-1032, 2008.
Mithen et al., "Development of isothiocyanate-enriched broccoli, and its enhanced ability to induce phase 2 detoxification enzymes in mammalian cells," Theor. and Appl. Genet. 106:727-734, 2003.
Reiter et al., "Global and local genome mapping in *Arabidopsis thaliana* by using recombinant inbred lines and random amplified polymorphic DNAs," Proc. Natl. Acad. Sci. USA 89:1477-1481, 1992.
Rozen et al., "Primer3 on the WWW for general users and for biologist programmers," Bioinformatics Methods and Protocols: Methods in Molecular Biology 132:365-386, 1999.
Sarikamis et al., "Evaluation of an SSR Marker for Marker-Assisted Selection in Kale (*Brassica oleracea* var. *acephala*)," Bulgarian Journal of Agricultural Science 16(1):36-41, 2010.
Sarikamis et al., "High glucosinolate broccoli: a delivery system for sulforaphane," Mol. Breeding 18(3):219-228, 2006.
Siebert et al., "An improved PCR method for walking in uncloned genomic DNA," Nucleic Acids Research 23 (6):1087-1088, 1995.
Traka et al., "Genetic regulation of glucoraphanin accumulation in Beneforte broccoli," New Phytologist, 198 (4):1085-1095, 2013.
Wentzell et al., "Linking Metabolic QTLs with Network and cis-eQTLs Controlling Biosynthetic Pathways," PLOS Genetics 3(9):1687-1701, 2007.
Zang et al., "Genome-wide identification of glucosinolate synthesis genes in *Brassica rapa*," FEBS Journal 276 (13):3559-3574, 2009.
NZ Intellectual Property Office; Office Action issued in New Zealand Patent Application No. 615094, dated Nov. 26, 2014.
Office Action issued in Chinese Patent Application No. 201310429742.1, dated Dec. 15, 2016.
Extended European Search Report regarding Europe Application No. 19210871.0, mailed Feb. 28, 2020.
Extended European Search Report regarding EP App. No. 22202212.1, dated May 3, 2023.

* cited by examiner

FIG. 5

```
The B.oleracea lines sequenced to create this consensus are:
GD33
breeder line 560216
breeder ID field number 2153.

The lines that contain the FT69 allele and were used to create this consensus are:
Breeder line 560526
Breeder line 580333
Breeder line BRM 51-1162
Breeder line BRM51-1210

FT69        1    GAAAATCACAGTTCACGCCTCTTACTCCATGAGCTTCTCTATTCTCATCC
Oleracea    1    GAAAATCACAGTTCACGCCTCTTACTCCATGAGCTTCTCTATTCTCATCC FT69       51    TAGTGTTATAATCTTGCAAACACATATAGAAAGCAAC TTTGGAGTGTAC
Oleracea   51    TAGTGTTATAATCTTGCAAACACATATAGAAAGCAAC TTTGGAGTGTAC FT69      101    GAGAAAAACATGAAAACACCTAGAAGCTCTGTGGGT AGACCCAAGAGCG
Oleracea  101    GAGAAAAACATGAAAACACCTAGAAGCTCTGTGGGT AGACCCAAGAGCG FT69      151    TTTCTCGATTAGTTTCATATACAGATGCATCAGAGTTCTCATCAACCGAT
Oleracea  151    TTTCTCGATTAGTTTCATATACAGATGCATCAGAGTTCTCATCAACCGAT FT69      201    CTACTTCTTTCTTATCTTATTAGAA AAAAAAATCCTATCAAAATTTACT
Oleracea  201    CTACTTCTTTCTTATCTTATTAGAA AAAAAAATCCTATCAAAATTTACT FT69      251    TTCCTGCAAGTATATTTTTCTTTACATTTTCATTTTCTTGAGTGTTATTT
Oleracea  251    TTCCTGCAAGTATATTTTTCTTTACATTTTCATTTTCTTGAGTGTTATTT FT69      301    GAGTGAAGTTATATTAAAATATT        GTTCATATATATCGAAAAT
Oleracea  301    GAGTGAAGTTATATTAAAATATT        GTTCATATATATCGAAAAT FT69      351    GTCAAGAAAGCCATGTTGTGTCGGAGAAGGGCTGAAGAAAGGGGCATGGA
Oleracea  351    GTCAAGAAAGCCATGTTGTGTCGGAGAAGGGCTGAAGAAAGGGGCATGGA FT69      401    CCACCGAGGAAGATAAGAAACTCATCTCTTACATCCATGAACATGGAGAA
Oleracea  401    CCACCGAGGAAGATAAGAAACTCATCTCTTACATCCATGAACATGGAGAA FT69      451    GGAGGCTGGCGCGACATTCCTCAAAAAGCTGGTTAATATCTATTATATAT
Oleracea  451    GGAGGCTGGCGCGACATTCCTCAAAAAGCTGGTTAATATCTATTATATAT FT69      501    TTTTTGGTAAATTTTTAAAAC ATATATGTTTGTTGGTATTTGATGTA
Oleracea  501    TTTTTGGTAAATTTTTAAAAC ATATATGTTTGTTGGTATTTGATGTA FT69      551    TGAAAGTTTTAT TTGAATGTGGTGTTTTACTAGGATTGAAAAGGTGTGG
Oleracea  551    TGAAAGTTTTAT TTGAATATGGTGTTTTACTAGGRTTGAAAAGGTGTGG FT69      601    AAAGAGTTG AGACTGCGATGGACTAACTACCTAAAACCTGAGATCAAAA
Oleracea  601    AAAGAGTTG AGACTGCGATGGACTAACTACCTAAAACCTGAGATCAAAA FT69      651    GAGGCGAGTTTAGTTCAGAGGAGGAACAGATTATCATCATGCTCCATGCT
Oleracea  651    GAGGCGAGTTTAGTTCAGAGGAGGAACAGATTATCATCATGCTCCATGCT FT69      701    GCTCGTGGCAACAAGTACGTTTATTTTAGACCAAAAAAAAACAAGTACGT
Oleracea  701    GCTCGTGGCAACAAGTACGTTTATTTTAGACCAAAAAAAAACAAGTACGT FT69      751    TTATTTTTAACAAAAAGGACGATTATATATTTT  TGTGTGTATGGATCC
Oleracea  751    TTATTTTTAACAAAAAGGACGATTATATATTTT  TGTGTGTATGGATCC FT69      801    TCCAGTGATCATCATTCTAGTTTTCTCTT TTTTTT ATACCGCAAACA
Oleracea  801    TCCAGTGATCATCATTCTAGTTTTCTCTT TTTTTT ATACCGCAAACA FT69      851    AATTTCATTAGTAAAAAAA TTAAAATTCCAAAGTCAATATTCAAAAACA
Oleracea  851    AATTTCATTAGTAAAAAAA TTAAAATTCCAAAGTCAATATTCAAAAACA

FT69      901    CAGTGTTATATA    ATCCTATATATGTCATATATTAAAAAAGTA
```

FIG. 5 continued

```
Oleracea  901 CAGTGTTATATA▒▒▒▒ATCCTATATATGTCATATATTAAAAAAGTA▒▒▒▒

FT69      951 ▒▒▒▒▒▒▒▒CAACATGAGAAATGAATTTAAGTATGCTTCTAAAGCGAAGT
Oleracea  951 ▒▒▒▒▒▒▒▒CAACATGAGAAATGAATTTAAGTATGCTTCTAAAGCGAAGT FT69     1001 TTTACTTCCC▒AAAAATTATTCTTTATTTTTTTCATGTATTTGACAATTC
Oleracea 1001 TTTACTTCCC▒AAAAATTATTCTTTATTTTTTTCATGTATTTGACAATTC FT69     1051 TCTGATGCAAAATATGTGTTTGATTAGCAATATGTGACTAAAAATTGCAA
Oleracea 1051 TCTGATGCAAAATATGTGTTTGATTAGCAATATGTGACTAAAAATTGCAA FT69     1101 TAGCACACATCATTTTAGTCTCTATTCCATA▒AAAAGCTTCAAAATAAAT
Oleracea 1101 TAGCACACATCATTTTAGTCTCTATTCCATA▒AAAAGCTTCAAAATAAAT FT69     1151 TTGATTAACTTTGGTCTTCCATCTTATCTCTTTCACTATTCTTGTCTTTA
Oleracea 1151 TTGATTAACTTTGGTCTTCCATCTTATCTCTTTCACTATTCTTGTCTTTA FT69     1201 GGTGGTCGGTCATAGCKAGACATTTACCTAGAAGAACMGACAATGAGATC
Oleracea 1201 GGTGGTCGGTCATAGCKAGACATTTACCTAGAAGAACMGACAATGAGATC FT69     1251 AAGAAYTACTGGAACACACATCTCAAGAAACGTTTGATCGAACAGGGTAC
Oleracea 1251 AAGAACTACTGGAACACACATCTCAAGAAACGTTTGATCGAACAGGGTAC FT69     1301 TGATCCCGTGACTCACAAGCCACTAGCTTCTAATACAAACCCTACTGTAC
Oleracea 1301 TGATCCCGTGACTCACAAGCCACTAGCTTCTAATACAAACCCTACTGTAC FT69     1351 CTGAGAATTTGCATTCCCTAGATGCATCTAG▒▒▒TTCCGACAAGCAATAC
Oleracea 1351 CTGAGAATTTGCATTCCCTAGATGCATCTAG▒▒▒TTCCGACAAGCAATAC FT69     1401 TCCCGGTCAAGCTCAATGCCTTCCATGTCTTGTACTCCTTCCTCCGGTTT
Oleracea 1401 TCCCGGTCAAGCTCAATGCCTTCCATGTCTTGTACTCCTTCCTCCGGTTT FT69     1451 CAACACGGTTTTCGAGAATACCAGCAAAGATGGGACACCAGTTCGTGAGG
Oleracea 1451 CAACACGGTTTTCGAGAATACCAGCAAAGATGGGACACCAGTTCGTGAGG FT69     1501 ACGATTCCTTGAGTCGCAAGAAACGTTT▒AAGAAATCAAGTTCTACATCA
Oleracea 1501 ACGATTCCTTGAGTCGCAAGAAACGTTT▒AAGAAATCAAGTTCTACATCA FT69     1551 AGGCTTTTGAACAAAGTTGCGGCTAAGGCCACTTCCATGAAA▒AAGCTTT
Oleracea 1551 AGGCTTTTGAACAAAGTTGCGGCTAAGGCCACTTCCATGAAA▒AAGCTTT FT69     1601 GTCTGCTTCCATGGAAGGTAG▒TTGAATGCTAATA▒AAGCTTTTCCAATG
Oleracea 1601 GTCTGCTTCCATGGAAGGTAG▒TTGAATGCTAATA▒AAGCTTTTCCAATG FT69     1651 GCTACTCTGAGCAGATTCTCAATGAAGATGATAGTTCTAATGCATCCCTC
Oleracea 1651 GCTACTCTGAGCAGATTCTCAATGAAGATGATAGTTCTAATGCATCCCTC FT69     1701 ATAAACACTCTCGCCGAGTTCGATCCCTTCCTCCAAACAACGTTTTACCC
Oleracea 1701 ATAAACACTCTCGCCGAGTTCGATCCCTTCCTCCAAACAACGTTTTACCC FT69     1751 TGAGAATGAGATGAATACTACTTCTGATCTCGGTATAGATCAGGACTACT
Oleracea 1751 TGAGAATGAGATGAATACTACTTCTGATCTCGGTATAGATCAGGACTACT FT69     1801 TCTCACATTTTCTCGAAAATTTCGGCA▒▒▒▒▒▒▒▒ACCA▒AATGAGGAG
Oleracea 1801 TCTCACATTTTCTCGAAAATTTCGGCA▒▒▒▒▒▒▒▒ACCA▒AATGAGGAG FT69     1851 CACTACATGAATCATAACTATGGTCATG▒TCTTCTTATGTCC▒ATGTGTC
Oleracea 1851 CACTACATGAATCATAACTATGGTCATG▒TCTTCTTATGTCC▒ATGTGTC FT69     1901 CCAAGAAGTCTCATCAACTAGCGTTGATGATCAAGACAATACTAATGAGG
Oleracea 1901 CCAAGAAGTCTCATCAACTAGCGTTGATGATCAAGACAATACTAATGAGG FT69     1951 GTTGGTCAAATTATCTTCTTGACCATGCTGATTTTATACATGACATGGAT
Oleracea 1951 GTTGGTCAAATTATCTTCTTGACCATGCTGATTTTATACATGACATGGAT FT69     2001 TCTGATTCCCTCGGAAAGCATCTCATATGAATCTTCGTGCC▒AAGCAGAA
Oleracea 2001 TCTGATTCCCTCGGAAAGCATCTCATATGAATCTTCGTGCC▒AAGCAGAA FT69     2051 AGGTTTCAAACT▒▒▒▒▒▒TGTCAGAACAAGAAGTTATGTATGTATTC
Oleracea 2051 AGGTTTCAAACT▒▒▒▒▒▒TGTCAGAACAAGAAGTTATGTATGTATTC
```

FIG. 5 continued

```
FT69     2101 TATTATATGGATTGTTTAGTATATGTCCAAGATCATGGTTGTTAGTCCCA
Oleracea 2101 TATTATATGGATTGTTTAGTATATGTCCAAGATCATGGTTGTTAGTCCCA FT69     2151 AGTTTAGGGTTTGTATAATATACAATAAGGGACGTTATCTTATAAAACGA
Oleracea 2151 AGTTTAGGGTTTGTATAATATACAATAAGGGACGTTATCTTATAAAACGA FT69     2201 GG
Oleracea 2201 GG
```

BRASSICA OLERACEA PLANTS WITH IMPROVED NUTRITIONAL VALUE

CROSS REFERENCE TO RELATED APPLICATIONS

This application is a divisional of U.S. patent application Ser. No. 17/175,280, filed Feb. 12, 2021, which is a continuation of co-pending U.S. application Ser. No. 16/431,310, filed Jun. 4, 2019, now U.S. Pat. No. 10,982,220, which is a divisional of U.S. application Ser. No. 15/359,429, filed Nov. 22, 2016, now U.S. Pat. No. 10,385,353, which is a continuation of U.S. application Ser. No. 14/025,512, filed Sep. 12, 2013, now U.S. Pat. No. 9,617,554, which claims benefit of U.S. provisional application No. 61/700,762, filed Sep. 13, 2012, each of which is herein incorporated by reference in their entireties.

INCORPORATION OF SEQUENCE LISTING

The sequence listing that is contained in the file named "SEMB008USD2 ST26.xml", which is 14.3 kilobytes as measured in Microsoft Windows operating system and was created on Nov. 7, 2023, is filed electronically herewith and incorporated herein by reference.

BACKGROUND OF THE INVENTION

1. Field of the Invention

The present invention relates to the development and use of *Brassica oleracea* plants with a recombined chromosomal segment.

2. Description of Related Art

Glucosinolates are allelochemicals present in 16 families of plant species, especially in Brassicaceae, of which broccoli is a notable example. Although there are over 120 different glucosinolates identified in nature, closely related taxonomic groups typically contain only a small number of such compounds. Glucosinolates that are dominant in broccoli such as glucoraphanin and glucoiberin are derived biochemically from the amino acid methionine. In the glucosinolate pathway, methionine is converted to homo-methionine and dihomomethionine by the activity of the ELONG (elongation) locus by adding a single carbon unit to the tail each time. Homo-methionine is eventually converted to 3-methylthiopropyl glucosinolate (glucoiberin; "MSP") while dihomo-methionine is converted to 4-methylthiobutyl glucosinolate (glucoraphanin; "MSB"). These glucosinolates (glucoiberin and glucoraphanin) are potent inducers of phase II detoxification enzymes, such as glutathione-S-transferase and quinone reductase, which promote the metabolism and excretion of potential carcinogens.

SUMMARY OF THE INVENTION

In one aspect, the present invention provides a *Brassica oleracea* plant comprising a Myb28 allele from *Brassica villosa* and lacking an ELONG allele from *Brassica villosa* genetically linked to said Myb28 allele, wherein the Myb28 allele confers elevated glucosinolates when compared to a plant that lacks the Myb28 allele.

In one embodiment, the plant is a broccoli plant. In other embodiments, the plant is inbred or hybrid. In another embodiment, the plant is homozygous for said Myb28 allele from *Brassica villosa*. In yet another embodiment, the plant is heterozygous for said Myb28 allele from *Brassica villosa*. In still another embodiment, the ELONG allele is from *Brassica oleracea*.

In another aspect, the present invention provides a part of a plant of the invention. In some embodiments, the plant part may further be defined as a leaf, an ovule, a floret, pollen, a head, or a cell.

In yet another aspect, the present invention provides a seed that produces a plant of the invention.

In still another aspect, the present invention provides a *Brassica oleracea* plant comprising a chromosomal segment that comprises a Myb28 allele from *Brassica villosa* and lacking an ELONG allele from *Brassica villosa* genetically linked to said Myb28 allele, wherein the segment confers elevated glucosinolates relative to a plant lacking the Myb28 allele, and wherein a sample of seed comprising the chromosomal segment was deposited under ATCC Accession Number PTA-13165. In one embodiment, the invention provides a seed that produces such a plant. In another embodiment, the invention provides a plant part, wherein the part is a leaf, an ovule, a floret, pollen, a head, or a cell. In another embodiment the plant is a *B. oleracea* plant.

In another aspect of the present invention a recombined DNA segment comprising a Myb28 allele from *Brassica villosa* and an ELONG allele from *Brassica oleracea* is provided. In one embodiment, the DNA segment is further defined as comprised within a cell. In another embodiment, the DNA segment is further defined as comprised within a seed. In yet another embodiment, the DNA segment is further defined as comprised within a plant.

In another aspect, the present invention provides a method for obtaining a *Brassica* plant comprising a desired glucosinolate composition comprising: a) obtaining a *Brassica* plant heterozygous for a Myb28 allele from *Brassica villosa* that confers elevated glucosinolates and is genetically linked in the plant to an ELONG allele from *Brassica villosa*; (b) obtaining progeny of the plant; and (c) selecting at least a first progeny plant in which recombination has occurred such that the progeny comprises the Myb28 allele but not the ELONG allele from *Brassica villosa*, wherein the progeny plant possesses a desired glucosinolate composition as a result of the presence of the Myb28 allele but not the ELONG allele from *Brassica villosa*.

In one embodiment, selection of the progeny plant comprises identifying a progeny plant that (1) comprises a genetic marker genetically linked to the Myb28 allele in *Brassica villosa* and/or lacks a genetic marker present at the corresponding locus in said *Brassica* plant, and (2) lacks a genetic marker genetically linked to the ELONG allele from *Brassica villosa* and/or comprises a genetic marker present at the corresponding locus from said *Brassica* plant.

In another embodiment, selection of the progeny plant comprises detecting a polymorphism that is found in the genome of said plant flanked by the complements of SEQ ID NO:1 and SEQ ID NO:2. In a further embodiment, such allele(s) are detected by a PCR-based method using oligonucleotide primer pair(s). In another embodiment, selection of the progeny plant comprises detecting a polymorphism in said progeny plant that is shown in FIG. 5. In a further embodiment, the *Brassica* plant may be a *B. oleracea* plant.

In yet a further aspect, the invention provides a plant produced by a method of the invention or a progeny thereof comprising the Myb28 allele but not the ELONG allele from *Brassica villosa*. In one embodiment, the invention provides a part of such a plant. In another embodiment, the part of the plant is selected from the group consisting of a cell, a seed, a root, a stem, a leaf, a head, a flower, and pollen.

In another aspect, the invention provides a method for producing a hybrid *Brassica oleracea* plant with elevated glucosinolate content comprising crossing a first *Brassica oleracea* parent plant with a second *Brassica oleracea* plant of a different genotype, wherein the first parent plant comprises a Myb28 allele from *Brassica villosa* that lacks an ELONG allele from *Brassica villosa* genetically linked to said Myb28 allele, wherein the Myb28 allele confers elevated glucosinolates relative to a plant lacking the Myb28 allele. In one embodiment, the method further comprises producing a plurality of hybrid *Brassica oleracea* plants comprising crossing the first *Brassica oleracea* parent plant with a plurality of second *Brassica oleracea* plants of different genotypes.

In still another aspect, the invention provides a method of producing a *Brassica oleracea* plant with a desired elevated glucosinolate content comprising introgressing into the plant a chromosomal segment comprising a Myb28 allele from *Brassica villosa* and lacking an ELONG allele from *Brassica villosa* genetically linked to said Myb28 allele, wherein segment confers a desired glucosinolate content relative to a plant lacking the segment, wherein a sample of seed comprising the chromosomal segment is deposited under ATCC Accession No. PTA-13165.

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

Other objects, features and advantages of the present invention will become apparent from the following detailed description. It should be understood, however, that the detailed description and any specific examples provided, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 5 shows an alignment between a consensus sequence of the Myb28 locus from *B. villosa* contained in broccoli variety FT69, and a consensus sequence of the corresponding locus from broccoli without increased level of glucosinolate, e.g. *B. oleracea*, (*Oleracea*) (SEQ ID NOs.: 8-9).

DETAILED DESCRIPTION OF THE INVENTION

Figure 1:
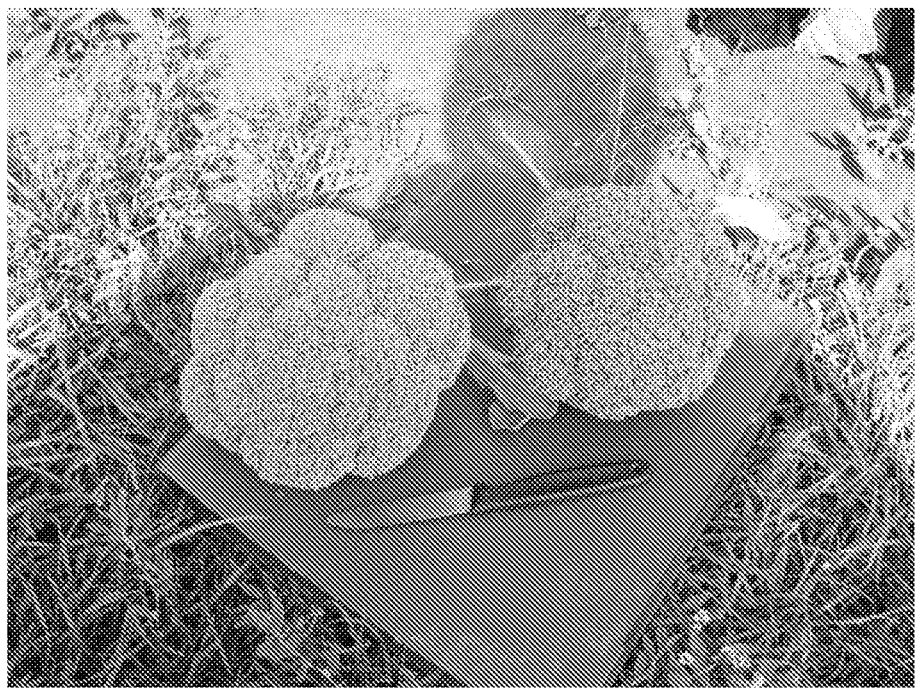
FIG. 1 depicts the head from hybrid broccoli varieties Ironman (left) and RX05991199 (right). Varieties were grown in Summer at a spacing of 50×50 cm.
Figure 2:
FIG. 2 shows a horizontal cross section of stems from hybrid broccoli varieties Ironman (left) and RX05991199 (right). Varieties were grown in Autumn at a spacing of 50×50 cm.
Figure 3:
FIG. 3 shows a profile of the head and stem from hybrid broccoli varieties Ironman (left) and RX05991199 (right). Varieties were grown in Autumn at a spacing of 50×50 cm.

The invention provides methods and compositions relating to plants, seeds and derivatives of *Brassica oleracea* plants comprising a new recombined introgression from *Brassica villosa* capable of conferring elevated 4-methylsulfinylbutyl glucosinolates (MSB), also known as glucoraphanin. It was also surprisingly found that plants comprising the introgression were capable of consistently producing hybrids that exhibited elevated glucoraphanin content relative to glucoiberin, while results were substantially more variable when using a parent line comprising the non-recombined introgression, such as in the case of the Myb28 donor parent of the hybrid PS05151639, which comprises Myb28 and ELONG alleles from *Brassica villosa* (US Patent Appln Pub No. 2011/0055945). The ability to produce multiple elite hybrid progeny with elevated glucoraphanin content and/or ratio of glucoraphanin to glucoiberin from a single inbred parent is significant in that the number of elite *Brassica oleracea* parent lines available to produce hybrid varieties is limited. The reduced introgression therefore substantially increases the utility of a given inbred and allows, for example, the production of multiple hybrids potentially adapted to different growing environments, end uses, or other criteria, each having a desired glucoraphanin content.

The new "reduced introgression" comprising a Myb28 locus from *Brassica villosa* and lacking the ELONG locus of *Brassica villosa* that has to date been genetically linked thereto is capable of consistently conferring in hybrids derived from a plant comprising the introgression elevated glucoraphanin relative to glucoiberin. One aspect of the current invention thus concerns methods for obtaining a *Brassica oleracea* plant comprising at least one such reduced introgression, wherein the resulting *Brassica oleracea* plant and/or progeny derived therefrom displays a desired glucoraphanin content relative to a control plant lacking the introgression. The invention thus provides plants possessing a desired glucoraphanin content conferred by a reduced introgression of the invention. In certain embodiments, methods for obtaining such plants comprise obtaining a *Brassica oleracea* plant heterozygous for a Myb28 allele from *Brassica villosa* that confers elevated glucosinolates and is genetically linked in the plant to an ELONG allele from *Brassica villosa*, obtaining progeny from such a plant, and selecting one or more such progeny plants wherein genetic recombination has occurred such that the progeny comprises an Myb28 allele from *Brassica villosa*, but does not comprise an ELONG allele from *Brassica villosa*. Such progeny or further progeny thereof may also possess a desired glucoraphanin content as a result of the presence of the Myb28 allele but not the ELONG allele from *Brassica villosa*. In particular embodiments, the method may comprise obtaining a progeny plant that comprises such allele(s) by identifying one or more genetic markers genetically linked to the Myb28 and/or ELONG allele(s). Identifying the genetic markers may comprise a phenotypic, a genetic, or a biochemical test, and may include screening a parent and/or progeny plant for the presence of, for instance, one or more allele described herein, including, for example, a Myb28 allele from *B. villosa*, an ELONG allele from *B. villosa* and an ELONG allele from *B. oleracea*.

Certain traits such as a glucoraphanin content relative to glucoiberin content, or the unpredictability of the type of glucosinolates in hybrid progeny heterozygous for a *Brassica villosa* Myb28 allele, were found to co-locate with a glucosinolate trait in the Myb28 allele from *Brassica villosa* and ELONG allele from *Brassica villosa* introgressions. Thus, formation of a "reduced" introgression is understood to be caused by recombination event(s) in the vicinity of the Myb28 and ELONG QTL(s). Lines comprising a reduced introgression, i.e., which have undergone a recombination event close to the QTL having elevated glucosinolates may efficiently be screened by use of molecular and/or phenotypic markers. Thus, plant populations or progeny of such populations, segregating (i.e., heterozygous) with respect to the QTL specified by Myb28 and ELONG introgressions, may be screened for plants having a recombinant phenotype, e.g. elevated glucoraphanin levels relative to glucoiberin levels.

In other embodiments, a method of the invention may comprise identifying a *Brassica oleracea* plant comprising a *Brassica villosa*-derived reduced introgression, and comprising a meiotic recombination between Myb28 and ELONG alleles as described herein. In particular embodiments, identifying the introgression may comprise measuring glucoraphanin and/or glucoiberin using standard protocols. In certain embodiments, a plant of the invention comprising a reduced introgression as disclosed herein comprises an elevated average proportion of glucoraphanin relative to glucoiberin compared to a plant comprising Myb28 and ELONG alleles from *Brassica villosa*, or a plant lacking a Myb28 allele from *Brassica villosa*. In one embodiment, such a plant comprising an elevated average proportion of glucoraphanin relative to glucoiberin is an inbred line, and in another embodiment is defined as a F1 hybrid having as one or more parent a plant comprising a reduced introgression of the invention. In particular embodiments, a plant of the invention is provided comprising a ratio of glucoraphanin to glucoiberin of about 10:1, 12:1, 15:1, 18:1, 20:1, 23:1, 25:1, 28:1, 30:1, 35:1 and about 40:1. In one aspect, an increase in glucoraphanin content may be calculated in reference to a standard *Brassica oleracea* variety, such as the broccoli variety Ironman.

A. Breeding of *Brassica oleracea* Lines Displaying Elevated Glucoraphanin

One aspect of the current invention concerns methods for crossing a plant comprising a reduced Myb28/ELONG introgression provided herein with itself or a second plant and the seeds and plants produced by such methods. These methods can be used for production and propagation of cultivated *Brassica oleracea* plants displaying desired glucosinolate compositions, including MSB and/or MSP content. Yet further, the plants of the current invention having elevated glucosinolate content comprise improved nutritional value of the plant relative to plants without elevated glucosinolates. The methods also can be used to produce hybrid *Brassica oleracea* seeds and the plants grown therefrom. Hybrid seeds are produced by crossing such lines with a second *Brassica oleracea* parent line. The hybrids may be heterozygous or homozygous for the reduced introgression.

*Brassica villosa* is a wild species endemic to northwest and central Sicily, and thus a Myb28 allele could be obtained by one of skill in the art from a plant selected from the wild. Alternatively, Myb28 alleles are known in the art and may be obtained from other sources for use with the invention, including SNR 347 (FT69; referred to as 428-11-69 in Mithen et al., *Theor Appl Genet*, 106:727-734; 2003), BR384-014, SNP13 (580333), SNP88 (BRM51-1210), BR384-020, B1639 (ATCC Accession Number PTA-9676), BRM51-1162 (ATCC Accession Number PTA-9675) and RX 05991199 (ATCC Accession No. PTA-13165). In accordance with the invention, a plant provided herein will generally lack an ELONG allele from *Brassica villosa* genetically linked to the Myb28 allele. This can be achieved according to the invention through crossing a plant comprising Myb28 and ELONG alleles from *Brassica villosa* with *Brassica* plants not comprising the Myb28 and ELONG alleles from *Brassica villosa*, including standard *Brassica oleracea* varieties. This includes the many broccoli varieties well known in the art, among others.

The goal of vegetable breeding is to combine various desirable traits in a single variety/hybrid. Such desirable traits may include any trait deemed beneficial by a grower and/or consumer, including greater yield, resistance to insects or disease, tolerance to environmental stress, and nutritional value. Breeding techniques used in an attempt to obtain desired traits take advantage of a plant's method of pollination. There are two general methods of pollination: a plant self-pollinates if pollen from one flower is transferred to the same or another flower of the same plant. A plant cross-pollinates if pollen comes to it from a flower of a different plant.

The development of uniform varieties requires the development of homozygous inbred plants, the crossing of these inbred plants, and the evaluation of the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines and hybrids derived therefrom are developed by selfing and selection of desired phenotypes.

In accordance with the invention, novel varieties may be created by crossing plants of the invention followed by generations of selection as desired and inbreeding for development of uniform lines. New varieties may also be created by crossing with any second plant. In selecting such a second plant to cross for the purpose of developing novel lines, it may be desired to choose those plants which either themselves exhibit one or more selected desirable characteristics or which exhibit the desired characteristic(s) when in hybrid combination. Once initial crosses have been made, inbreeding and selection take place to produce new varieties. For development of a uniform line, often five or more generations of selfing and selection are typically involved.

Uniform lines of new varieties may also be developed by way of doubled-haploids. This technique allows the creation of true breeding lines without the need for multiple generations of selfing and selection. In this manner true breeding lines can be produced in as little as one generation. Haploid embryos may be produced from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. In accordance with the invention, any of such techniques may be used in connection with a plant of the present invention and progeny thereof to achieve a homozygous line.

Backcrossing can also be used to improve an inbred plant. Backcrossing transfers a specific desirable trait, such as elevated glucoraphanin, from one inbred or non-inbred source to a variety that lacks that trait. This can be accomplished, for example, by first crossing a parent (A) (recurrent parent) to a donor inbred (non-recurrent parent), which carries the appropriate locus or loci for the trait in question. The progeny of this cross are then mated back to the recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the first parent for most or almost all other loci. The last backcross generation would be selfed to give pure breeding progeny for the trait being transferred.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. It may be necessary to introduce a test of the progeny to determine if the desired characteristic has been successfully transferred.

*Brassica oleracea* varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

Many single locus traits have been identified that are not regularly selected for in the development of a new inbred but that can be improved by backcrossing techniques. Single locus traits may or may not be transgenic; examples of these traits include, but are not limited to, male sterility, herbicide resistance, resistance to bacterial, fungal, or viral disease, insect resistance, restoration of male fertility, modified fatty acid or carbohydrate metabolism, and enhanced nutritional quality. These comprise genes generally inherited through the nucleus.

Direct selection may be applied where the single locus acts as a dominant trait. Selection of *Brassica* plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay which is able to identify the relative presence or absence of a trait of interest in a plant can also be useful for breeding purposes.

Procedures for marker assisted selection are of particular utility for introgression of given traits. Well known types of genetic markers that could be used in accordance with the invention include, but are not necessarily limited to, Simple Sequence Length Polymorphisms (SSLPs), Cleaved Amplified Polymorphic Sequences (CAPs), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs), and Single Nucleotide Polymorphisms (SNPs).

B. Plants Derived from a Plant of the Invention by Genetic Engineering

Many useful traits that can be introduced by backcrossing, as well as directly into a plant, are those, which may be introduced by genetic transformation techniques. Genetic transformation may therefore be used to insert a selected transgene into a *Brassica* plant of the invention or may, alternatively, be used for the preparation of transgenes, which can be introduced by backcrossing. Methods for the transformation of plants, including *Brassica*, are well known to those of skill in the art.

Vectors used for the transformation of plant cells are not limited so long as the vector can express an inserted DNA in the cells. For example, vectors comprising promoters for constitutive gene expression in *Brassica* cells (e.g., cauliflower mosaic virus 35S promoter) and promoters inducible by exogenous stimuli can be used. Examples of suitable vectors include pBI binary vector. The "*Brassica* cell" into which the vector is to be introduced includes various forms of *Brassica* cells, such as cultured cell suspensions, protoplasts, leaf sections, and callus.

A vector can be introduced into *Brassica* cells by known methods, such as the polyethylene glycol method, polycation method, electroporation, *Agrobacterium*-mediated transfer, particle bombardment and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

One efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded can be positioned at an appropriate distance below the macroprojectile stopping plate. Microprojectile bombardment techniques are widely applicable, and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium* (and other *Rhizobia*), allowing for convenient manipulations. Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (U.S. Pat. No. 5,563,055). For example, U.S. Pat. No. 5,349,124 describes a method of transforming plant cells using *Agrobacterium*-mediated transformation. By inserting a chimeric gene having a DNA coding sequence encoding for the full-length B.t. toxin protein that expresses a protein toxic toward Lepidopteran larvae, this methodology resulted in plants having resistance to such insects.

A number of promoters have utility for plant gene expression for any gene of interest including but not limited to selectable markers, scorable markers, genes for pest tolerance, disease resistance, nutritional enhancements and any other gene of agronomic interest. Examples of constitutive promoters useful for *Brassica* plant gene expression include, but are not limited to, the cauliflower mosaic virus (CaMV) P-35S promoter, which confers constitutive, high-level expression in most plant tissues, including monocots; a tandemly duplicated version of the CaMV 35S promoter, the enhanced 35S promoter (P-e35S) the nopaline synthase promoter, the octopine synthase promoter; and the figwort mosaic virus (P-FMV) promoter as described in U.S. Pat. No. 5,378,619 and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

Exemplary nucleic acids which may be introduced to the plants of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a *Brassica* plant according to the invention. Non-limiting examples of particular genes and corresponding phenotypes one may choose to introduce into a *Brassica* plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference it their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms. The RNA could also be a catalytic RNA molecule (i.e., a ribozyme) engineered to cleave a desired endogenous mRNA product. Thus, any gene which produces a protein or mRNA which expresses a phenotype or morphology change of interest is useful for the practice of the present invention.

D. Definitions

In the description and tables herein, a number of terms are used. In order to provide a clear and consistent understanding of the specification and claims, the following definitions are provided:

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Cultivated Variety: A *Brassica oleracea* variety which is suitable for consumption and meets the requirements for commercial cultivation. An example is a broccoli variety. In addition to the plants themselves, and the parts thereof suitable for consumption, such as the heads or leaves, the invention comprises parts or derivatives of the plant suitable for propagation. Examples of parts suitable for propagation are organ tissues, such as leaves, stems, roots, shoots and the like, protoplasts, somatic embryos, anthers, petioles, cells in culture and the like. Derivatives suitable for propagation are for instance seeds. The plants according to the invention can be cultivated or propagated in the conventional manner but also by means of tissue culture techniques from plant parts.

Crossing: The mating of two parent plants.

Cross-pollination: Fertilization by the union of two gametes from different plants.

Diploid: A cell or organism having two sets of chromosomes.

Enzymes: Molecules which can act as catalysts in biological reactions.

$F_1$ Hybrid: The first generation progeny of the cross of two nonisogenic plants.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Marker: A readily detectable phenotype, preferably inherited in co-dominant fashion (both alleles at a locus in a diploid heterozygote are readily detectable), with no environmental variance component, i.e., heritability of 1.

Phenotype: The detectable characteristics of a cell or organism, which characteristics are the manifestation of gene expression.

Quantitative Trait Loci (QTL): Quantitative trait loci (QTL) refer to genetic loci that control to some degree numerically representable traits that are usually continuously distributed.

Recombination event is understood to mean a meiotic crossing-over.

Regeneration: The development of a plant from tissue culture.

Self-pollination: The transfer of pollen from the anther to the stigma of the same plant.

Single Locus Converted (Conversion) Plant: Plants which are developed by a plant breeding technique called backcrossing, wherein essentially all of the desired morphological and physiological characteristics of a broccoli variety are recovered in addition to the characteristics of the single locus transferred into the variety via the backcrossing technique and/or by genetic transformation.

Substantially Equivalent: A characteristic that, when compared, does not show a statistically significant difference (e.g., p=0.05) from the mean.

Tissue Culture: A composition comprising isolated cells of the same or a different type or a collection of such cells organized into parts of a plant.

Transgene: A genetic locus comprising a sequence which has been introduced into the genome of a broccoli plant by transformation.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

E. Deposit Information

A deposit was made of at least 2500 seeds of broccoli hybrid RX 05991199, which comprises a reduced introgression comprising a Myb28 allele from *Brassica villosa* and an ELONG allele from *Brassica oleracea*, as described herein. The deposit was made with the American Type Culture Collection (ATCC), 10801 University Boulevard, Manassas, Va. 20110-2209 USA. The deposit is assigned ATCC Accession No. PTA-13165. The date of deposit was Aug. 24, 2012. Access to the deposits will be available during the pendency of the application to persons entitled thereto upon request. The deposits will be maintained in the ATCC Depository, which is a public depository, for a period of 30 years, or 5 years after the most recent request, or for the enforceable life of the patent, whichever is longer, and will be replaced if nonviable during that period. Applicant does not waive any infringement of their rights granted under this patent or any other form of variety protection, including the Plant Variety Protection Act (7 U.S.C. 2321 et seq.).

EXAMPLES

Example 1

Development of Parent Lines with Improved MSB Profiles

One benefit of the current invention is that parent lines may be created comprising a reduced introgression of the invention, wherein the lines and hybrids derived therefrom exhibit an increased proportion of MSB/MSP and/or a greater stability of expression of MSB. The development of such a broccoli line comprising a Myb28/ELONG reduced introgression can be summarized as follows:

The line FT69, which has elevated levels of the phytochemical MSP (glucoiberin) as a result of the presence of Myb28 and ELONG loci from *B. villosa* (Mithen et al., 2003; *Theor. Appl. Genet.*, 106:727-734), was crossed with a breeding line designated BR9. The resulting progeny was crossed with the male parent from Ironman (BRM 56-3905 SI). F1 progeny were grown in replications in a Wageningen selection trial. From plots designated 408, 409, 410, 411 and 412, 89 plants were selected that were analyzed for glucoiberin (MSP) and glucoraphanin (MSB). Six plants with the highest MSB were selected.

All 6 plants were selfed and backcrossed with the recurrent parent BRM 56-3905 SI. The 6 selfings and 6 BC1 were planted in replicated selection trials in Wageningen. Each BC1 (where BC=backcross) had 2 plots with 24 plants/plot. From these 12 plots, a total of 84 plants were selected that most resembled the recurrent parent. Heads from these selections were sent for MSP and MSB analyses. Seven plants with highest MSB were kept for further selfing and BC. All 7 BC1 plants were selfed and backcrossed with the recurrent parent (BRM 56-3905 SI). Selfings and 5 BC2 populations were sown and selected in replicated Wageningen Autumn selection trials. A total of 73 plants that resembled the recurrent parent most were selected and sent for MSP/MSB analyses. Eight BC2 plants with highest MSB levels were kept for further selfing and BC.

All 8 BC2 plants were selfed and backcrossed with the recurrent parent (BRM 56-3905 SI). Four BC3 were obtained and planted in 1-4 replications in Wageningen. 47 plants closest to the recurrent parent were sent for MSP/MSB analyses. 7 BC3 plants with highest MSB levels were kept for further selfing and BC. All 7 BC3 plants were selfed and backcrossed with the recurrent parent (BRM 56-3905 SI). 6 BC4 were obtained and these were planted in selection trials. 54 plants closest to the recurrent parent were sent for MSP/MSB analyses. 8 BC4 plants with the highest MSB levels were kept for further selfing and BC.

All 8 BC4 plants were selfed. 7 BC4 plants produced selfed seed and the BC4F2 were planted in unreplicated Wageningen selection trials. 37 BC4F2 plants closest to the recurrent parent were selected and these were sent for MSP/MSB analyses. 4 BC4F2 plants with highest MSB levels were kept for further selfing and BC.

All 4 BC4F2 plants were selfed. All 4 produced selfed seed and the 4 BC4F3 were planted in unreplicated selection trials. 12 BC4F3 plants closest to the recurrent parent were selected and sent for MSP/MSB analyses. 4 BC4F2 plants with the highest MSB levels were kept for further selfing and BC. All selected plants from plot 1169 (570114) had equally high MSB level of average 2.3 mmol/kg, or about 5× the level of the standard reference variety (General). This indicated that the source has alleles fixed for high MSB.

All 3 selections from 1169 (BC4F3) were selfed. All 3 produced seed and these were planted in selection trials. SNP13-580333 (1169-1, A75-1) was the most uniform on type and 5 plants were selected for MSB check. All 5 had equally high levels of MSB of about 3.2 mmol/kg. 1169-1, also designated BRM 53-3934 SI, was put on tissue culture for increase and use as a male parent to RX-1199 (RX 05991199). An analysis of BRM 53-3934 SI revealed that it contained the Myb28 reduced introgression, which results in a parent line with the ability to consistently produce progeny with glucosinolates comprising an increased proportion of MSB/MSP relative to plants having the *B. villosa* ELONG locus, as shown below.

Example 2

Analysis of Hybrid Broccoli Lines Having Elevated Glucoraphanin

Self and outcrosses were made using different standard broccoli lines as female parents as shown in Table 1 in crosses with the following: (1) FT69 (high glucoiberin line with ELONG and Myb28 from *B. villosa*), (2) SNP13-580333 (high glucoraphanin line with ELONG from *B. oleracea* and Myb28 from *B. villosa*, as described above), and (3) SNP88-BRM51-1210 (high glucoiberin line ELONG and Myb28 from *B. villosa*). As can be seen, regular broccoli lines have a relatively low amount of total glucosinolates. The ratio between MSB and MSP is particularly shown to be depending on the regular broccoli female line in the case of FT69 (428-11-69), which comprises ELONG and Myb28 alleles from *B. villosa*. In contrast, in all the crosses with SNP13-580333 most of the glucosinolates are glucoraphanin. This indicates the benefit of the reduced introgression in consistently producing hybrid varieties comprising elevated glucoraphanin in crosses with multiple different second parents.

TABLE 1

Levels of Glucoraphanin Resulting From Different Crosses

| Female line (regular broccoli line) | Male self (self or crosses with different high glucosinolates sources) | Glucoiberin micromoles/ gramDWt | Glucoraphanin micromoles/ gramDWt | Ratio MSB/MSP |
| --- | --- | --- | --- | --- |
| BR384-014 | self | 3.31 | 18.74 | 5.66 |
| BR384-014 | FT69 (428-11-69) (contains Myb28 and ELONG from *B. villosa*) | 57.47 | 15.12 | 0.26 |
| BR384-014 | SNP13-580333 (BRM 53-3934 SI) (contains reduced introgression) | 3.77 | 40.14 | 10.65 |
| BR384-014 | SNP88-BRM51-1210 (contains Myb28 and ELONG from *B. villosa*) | 28.71 | 5.85 | 0.20 |
| BR384-020 | Self | 1.83 | 18.24 | 9.97 |
| BR384-020 | FT69 (428-11-69) | 36.72 | 10.00 | 0.27 |
| BR384-020 | SNP13-580333 | 2.34 | 26.29 | 11.23 |
| BR384-020 | SNP88-BRM51-1210 | 13.53 | 33.96 | 2.51 |
| BR384-024 | self | 1.59 | 3.64 | 2.29 |
| BR384-024 | FT69 (428-11-69) | 56.61 | 7.75 | 0.14 |
| BR384-024 | SNP13-580333 | 2.64 | 26.48 | 10.03 |
| BR384-024 | SNP88-BRM51-1210 | 22.11 | 3.24 | 0.15 |
| BR384-025 | self | 1.43 | 2.67 | 1.87 |
| BR384-025 | FT69 (428-11-69) | 39.66 | 6.39 | 0.16 |
| BR384-025 | SNP13-580333 | 3.52 | 27.55 | 7.83 |
| BR384-025 | SNP88-BRM51-1210 | 14.25 | 9.59 | 0.67 |
| BR384-026 | self | 1.74 | 5.08 | 2.92 |
| BR384-026 | FT69 (428-11-69) | 41.11 | 8.26 | 0.20 |
| BR384-026 | SNP13-580333 | 1.80 | 30.53 | 16.93 |
| BR384-026 | SNP88-BRM51-1210 | 19.52 | 2.89 | 0.15 |
| BR384-027 | self | 2.06 | 13.52 | 6.55 |
| BR384-027 | FT69 (428-11-69) | 9.32 | 47.34 | 5.08 |
| BR384-027 | SNP13-580333 | 2.60 | 27.47 | 10.57 |
| BR384-027 | SNP88-BRM51-1210 | 6.61 | 28.12 | 4.26 |
| BR384-033 | self | 0.57 | 16.88 | 29.42 |
| BR384-033 | FT69 (428-11-69) | 7.58 | 46.89 | 6.18 |
| BR384-033 | SNP13-580333 | 2.48 | 30.81 | 12.41 |
| BR384-033 | SNP88-BRM51-1210 | 5.23 | 28.75 | 5.49 |
| BR384-040 | self | 0.91 | 14.03 | 15.46 |
| BR384-040 | FT69 (428-11-69) | 4.77 | 45.61 | 9.56 |
| BR384-040 | SNP13-580333 | 1.56 | 16.02 | 10.27 |
| BR384-040 | SNP88-BRM51-1210 | 3.30 | 12.73 | 3.86 |

TABLE 1-continued

Levels of Glucoraphanin Resulting From Different Crosses

| Female line (regular broccoli line) | Male self (self or crosses with different high glucosinolates sources) | Glucoiberin micromoles/ gramDWt | Glucoraphanin micromoles/ gramDWt | Ratio MSB/MSP |
|---|---|---|---|---|
| BR384-044 | self | 0.81 | 11.94 | 14.74 |
| BR384-044 | FT69 (428-11-69) | 9.48 | 50.08 | 5.28 |
| BR384-044 | SNP13-580333 | 1.99 | 23.47 | 11.81 |
| BR384-044 | SNP88-BRM51-1210 | 5.19 | 27.95 | 5.38 |
| BR384-048 | FT69 (428-11-69) | 62.53 | 5.85 | 0.09 |
| BR384-048 | SNP13-580333 | 3.02 | 27.95 | 9.25 |
| BR384-048 | SNP88-BRM51-1210 | 18.99 | 1.24 | 0.07 |
| BR384-052 | self | 1.51 | 7.38 | 4.88 |
| BR384-052 | FT69 (428-11-69) | 8.27 | 38.54 | 4.66 |
| BR384-052 | SNP13-580333 | 2.43 | 24.09 | 9.92 |
| BR384-053 | self | 0.28 | 2.06 | 7.49 |
| BR384-053 | FT69 (428-11-69) | 7.30 | 53.95 | 7.39 |
| BR384-053 | SNP13-580333 | 0.64 | 21.64 | 33.74 |
| BR384-053 | SNP88-BRM51-1210 | 3.39 | 14.50 | 4.27 |
| BR384-057 | self | 1.43 | 3.79 | 2.64 |
| BR384-057 | FT69 (428-11-69) | 38.32 | 8.11 | 0.21 |
| BR384-057 | SNP13-580333 | 4.13 | 32.20 | 7.80 |
| BR384-057 | SNP88-BRM51-1210 | 20.38 | 3.47 | 0.17 |
| BR384-060 | self | 1.76 | 7.90 | 4.49 |
| BR384-060 | FT69 (428-11-69) | 10.62 | 42.68 | 4.02 |
| BR384-060 | SNP13-580333 | 2.76 | 26.06 | 9.46 |
| BR384-060 | SNP88-BRM51-1210 | 5.46 | 23.19 | 4.25 |
| BR384-061 | self | 0.99 | 15.47 | 15.65 |
| BR384-061 | FT69 (428-11-69) | 8.03 | 49.14 | 6.12 |
| BR384-061 | SNP13-580333 | 2.58 | 35.61 | 13.82 |
| BR384-061 | SNP88-BRM51-1210 | 5.92 | 36.02 | 6.09 |
| BR384-069 | self | 1.63 | 7.02 | 4.32 |
| BR384-069 | FT69 (428-11-69) | 9.33 | 56.09 | 6.01 |
| BR384-069 | SNP13-580333 | 1.44 | 26.36 | 18.32 |
| BR384-069 | SNP88-BRM51-1210 | 4.60 | 29.96 | 6.51 |
| BR384-078 | self | 1.23 | 7.59 | 6.15 |
| BR384-078 | FT69 (428-11-69) | 10.54 | 36.99 | 3.51 |
| BR384-078 | SNP13-580333 | 2.75 | 24.94 | 9.06 |
| BR384-078 | SNP88-BRM51-1210 | 5.74 | 23.42 | 4.08 |
| BR384-082 | self | 1.57 | 10.41 | 6.64 |
| BR384-082 | FT69 (428-11-69) | 10.67 | 38.80 | 3.64 |
| BR384-082 | SNP13-580333 | 2.53 | 29.25 | 11.55 |
| BR384-082 | SNP88-BRM51-1210 | 6.38 | 31.80 | 4.98 |
| BR384-083 | self | 1.31 | 8.44 | 6.45 |
| BR384-083 | FT69 (428-11-69) | 9.33 | 39.32 | 4.21 |
| BR384-083 | SNP13-580333 | 2.23 | 22.39 | 10.04 |
| BR384-083 | SNP88-BRM51-1210 | 4.85 | 21.90 | 4.52 |
| BR384-089 | self | 3.40 | 0.35 | 0.10 |
| BR384-089 | FT69 (428-11-69) | 48.47 | 7.21 | 0.15 |
| BR384-089 | SNP13-580333 | 4.67 | 24.59 | 5.27 |
| BR384-089 | SNP88-BRM51-1210 | 19.12 | 1.98 | 0.10 |

Example 3

Development of Broccoli Hybrids

As explained above, one embodiment of the invention comprises producing broccoli hybrids wherein one or both parents of the hybrid comprise a Myb28 reduced introgression and, as a result, exhibit an elevated MSB content and/or more stable MSB content relative to hybrids lacking a parent comprising the introgression. One example of such a hybrid that was produced is the hybrid RX 05991199. This hybrid was created by crossing parents BRM 53-3934 SI and BRM 56-3907 CMS, typically with BRM 53-3934 SI as a male parent. The production of BRM 53-3934 SI is described in Example 1 above. As explained, this parent contains the Myb28 reduced introgression. The female parent BRM 56-3907 CMS is a known inbred that served as the parent of the commercial hybrid "Ironman." BRM 56-3907 CMS is the subject of, and is described in, EU Plant Variety Rights Certificate #20341, granted Jun. 18, 2007.

A description of the physiological and morphological characteristics of broccoli hybrid RX 05991199 and the parent lines thereof is presented below.

TABLE 2

Physiological and Morphological Characteristics of Hybrid RX 05991199

| | Characteristic | RX05991199CMS | Ironman |
|---|---|---|---|
| A | Region of Adaptation | NW Europe | NW Europe |
| B | Maturity, Spring Planted | | |
| | days from direct seeding to 50% harvest | no direct seeding | no direct seeding |
| | days from transplanting to 50% harvest | 64 | 63 |
| | transplant date | 10 May 2010 | 10 May 2010 |
| | length of harvest period in days | 8 | 6 |
| | first harvest date | 12 Jul. 2010 | 12 Jul. 2010 |
| | last harvest date | 19 Jul. 2010 | 17 Jul. 2010 |
| | harvest season (main crop at 50% harvest) | summer | summer |
| | time of harvest maturity (50% of plants) | medium (Sumosun) | medium (Sumosun) |
| | time of beginning of flowering (50% of plants with at least 10% flowers) **choice for UPOV TG only | medium*8 (Coaster, Cruiser) | medium*8 (Coaster, Cruiser) |

TABLE 2-continued

Physiological and Morphological Characteristics of Hybrid RX 05991199

| | Characteristic | RX05991199CMS | Ironman |
|---|---|---|---|
| C | Seedling | | |
| | cotyledon color | medium green | medium green |
| | RHS color chart value for seedling cotyledon color | 147B | 147B |
| | cotyledon anthocyanin | intermediate | intermediate |
| | hypocotyl anthocyanin | strong | strong |
| D | Plant | | |
| | plant height in centimeters from soil line to top of leaves | 56.3 cm | 61.0 cm |
| | head height in centimeters from soil line to top of leaves | 33.7 cm | 34.7 cm |
| | height at harvest maturity | medium (Coaster) | medium (Coaster) |
| | number of stems | one (Ramoso Calabrese, Shogun) | one (Ramoso Calabrese, Shogun) |
| | branches | medium | few |
| | habit | intermediate | intermediate |
| | market class | fresh market | fresh market |
| | life cycle | annual | annual |
| | type of variety | first generation hybrid | first generation hybrid |
| E | Leaves | | |
| | outer leaves: number of leaves per plant (at harvest) | 14 | 17 |
| | outer leaves: width (at midpoint of plant including petiole) | 22.6 cm | 24.2 cm |
| | leaf: width | medium (Buccaneer, Green Belt) | medium (Buccaneer, Green Belt) |
| | outer leaves: length (at midpoint of plant including petiole) | 48.7 cm | 53.2 cm |
| | leaf: length (including petiole) | medium (Brigadeer, Sumosun) | long (Green Duke, Laser) |
| | outer leaves: petiole length | 22.1 cm | 24.9 cm |
| | petiole: length | medium (Emperor, Ramoso Calabrese) | long (Groene Calabrese, Premium Crop) |
| | outer leaves: leaf ratio—length/width | 2:1 | 2:1 |
| | outer leaves: leaf attachment | petiolate | petiolate |
| | outer leaves: wax presence | weak | intermediate |
| | leaf: number of lobes | medium (Coaster, Topper) | medium (Coaster, Topper) |
| | outer leaves: foliage color (with wax, if present) | grey green | grey green |
| | outer leaves: foliage color (with wax, if present; RHS color chart value) | 189A | 189A |
| | leaf blade: color | grey green (Bishop) | grey green (Bishop) |
| | leaf blade: intensity of color | dark | dark |
| | leaf blade: anthocyanin coloration | absent (Claudia, Embassy) | absent (Claudia, Embassy) |
| | leaf blade: undulation of margin | weak (Beaufort, Early Pack, Laser, Paladin) | weak (Beaufort, Early Pack, Laser, Paladin) |
| | leaf blade: dentation of margin | weak (Galaxy) | weak (Galaxy) |
| | outer leaves: leaf shape | elliptic | elliptic |
| | outer leaves: leaf base | blunt | blunt |
| | outer leaves: leaf apex | blunt | blunt |
| | outer leaves: leaf margins | slightly wavy | slightly wavy |
| | outer leaves: leaf veins | intermediate | intermediate |
| | outer leaves: midrib | slightly raised | not raised |
| | leaf blade: blistering | medium (Medium Late 145, Skiff) | medium (Medium Late 145, Skiff) |
| | outer leaves: attitude (leaf angle from ground) | semi-erect (35-55 degrees) | semi-erect (35-55 degrees) |
| | leaf: attitude (at beginning of head formation) | semi-erect (Arcadia, Asti, Civet, Claudia) | semi-erect |
| | outer leaves: torsion of leaf tip | none | none |
| | outer leaves: profile of upper side of leaf | planar | planar |
| F | Head | | |
| | length of branching at base (excluding stem) | very short (Viola) | very short (Viola) |
| | diameter at widest point (at market maturity) | 15.2 cm | 14.7 cm |
| | depth (at market maturity) | 9.7 cm | 9.4 cm |
| | weight, market trimmed (at market maturity) | 439.9 gm | 400.3 gm |
| | color | grey green (Brigadeer, Galaxy) | grey green (Brigadeer, Galaxy) |
| | intensity of color | medium | medium |
| | RHS color chart value for head color | 189B | 189B |
| | anthocyanin coloration | absent (Early White Sprouting) | present (Brigadeer, Shogun, Viola) |
| | shape (at market maturity) | transverse elliptic (Buccaneer, Futura) | transverse elliptic (Buccaneer, Futura) |
| | dome shape (at market maturity) | domed | domed |
| | size (at market maturity) for US Exhibit C only choice | medium (Dundee, Early Man) | medium** (Dundee, Early Man) |
| | compactness/firmness (at market maturity) | medium (Late Corona) | short pedicels/tight/firm (Captain) |
| | surface knobbling (at market maturity) | fine (Apollo, Brigadeer) | medium (Southern Comet) |
| | texture | medium (Clipper, Coaster) | fine (Auriga, Bishop, Green Top) |
| | bead size (at market maturity) | medium | small |
| | flower buds (at market maturity) | even in size | even in size |
| | anthocyanin coloration of leaf axils (at market maturity) | absent | absent |
| | anthocyanin coloration of leaf veins (at market maturity) | absent | absent |
| | anthocyanin coloration of leaf blade (at market maturity) | absent | absent |
| | anthocyanin coloration of entire plant (at market maturity) | absent | absent |
| | anthocyanin coloration of leaf petiole (at market maturity) | absent (Claudia, Embassy) | absent (Claudia, Embassy) |
| | color of head leaves (at market maturity) | green | green |
| | RHS color chart value for the color of head leaves | N189B | N189B |
| | bracts | absent (Gem, Orion) | absent (Gem, Orion) |
| | secondary heads (at market maturity) | combination, present** (Marathon, Tribute, Late Purple Sprouting) | present, combination |
| | prominence of secondary heads (at market maturity) | intermediate (Citation) | weak |
| | number of secondary heads (at market maturity) | 4 | 2 |
| G | Flower | | |
| | Color choice for UPOV TG only | yellow (Brigadeer, Orion) | yellow** (Brigadeer, Orion) |

TABLE 2-continued

Physiological and Morphological Characteristics of Hybrid RX 05991199

| Characteristic | RX05991199CMS | Ironman |
|---|---|---|
| intensity of yellow color | medium (Capitol, Corvet) | medium (Capitol, Corvet) |
| color | 4B | 4B |
| stalk color | green | green |
| RHS color chart value for flower stalk color | 138B | 138B |
| male sterility | present (Chevalier, Montop) | present (Chevalier, Montop) |

*These are typical values. Values may vary due to environment. Other values that are substantially equivalent are also within the scope of the invention.

TABLE 3

Physiological and Morphological Characteristics of Line BRM 53-3934 SI

| | Characteristic | BMR53-3934SI | Sibsey |
|---|---|---|---|
| A | Region of Adaptation | NW Europe | NW Europe |
| B | Maturity, Spring Planted | | |
| | days from direct seeding to 50% harvest | no direct seeding | no direct seeding |
| | days from transplanting to 50% harvest | 76 | 54 |
| | transplant date | 10 May 2010 | 10 May 2010 |
| | length of harvest period in days | 16 | 5 |
| | first harvest date | 17 Jul. 2010 | 1 Jul. 2010 |
| | last harvest date | 1 Aug. 2010 | 5 Jul. 2010 |
| | harvest season (main crop at 50% harvest) | summer | summer |
| | time of harvest maturity (50% of plants) | very late (Late Purple Sprouting) | very early (Earlyman, Primor) |
| | time of beginning of flowering (50% of plants with at least 10% flowers) choice for UPOV TG only | late (Shogun, Viola) | early** (Clipper, Southern Comet) |
| C | Seedling | | |
| | cotyledon color | medium green 147B | medium green 147B |
| | RHS color chart value for seedling cotyledon color | | |
| | cotyledon anthocyanin | weak | intermediate |
| | hypocotyl anthocyanin | weak | intermediate |
| D | Plant | | |
| | plant height in centimeters from soil line to top of leaves | 51.7 cm | 55.0 cm |
| | head height in centimeters from soil line to top of leaves | 30.3 cm | 50.0 cm |
| | height at harvest maturity | medium (Coaster) | medium (Coaster) |
| | number of stems | one (Ramoso Calabrese, Shogun) | one (Ramoso Calabrese, Shogun) |
| | branches | medium | many |
| | habit | compact | compact |
| | market class | fresh market | fresh market |
| | life cycle | annual | annual |
| | type of variety | inbred | first generation hybrid |
| E | Leaves | | |
| | outer leaves: number of leaves per plant (at harvest) | 20 | 12 |
| | outer leaves: width (at midpoint of plant including petiole) | 21.8 cm | 18.9 cm |
| | leaf: width | medium (Buccaneer, Green Belt) | narrow (Arcadia, Brigadeer) |
| | outer leaves: length (at midpoint of plant including petiole) | 45.3 cm | 39.1 cm |
| | leaf: length (including petiole) | medium (Brigadeer, Sumosun) | short (Dandy Early, Emperor) |
| | outer leaves: petiole length | 20.2 cm | 16.0 cm |
| | petiole: length | medium (Emperor, Ramoso Calabrese) | short (High Sierra, Padovano) |
| | outer leaves: leaf ratio—length/width | 2:1 | 2:1 |
| | outer leaves: leaf attachment | petiolate | petiolate |
| | outer leaves: wax presence | intermediate | intermediate |
| | leaf: number of lobes | medium (Coaster, Topper) | medium (Coaster, Topper) |
| | outer leaves: foliage color (with wax, if present) | blue green | grey green |
| | outer leaves: foliage color (with wax, if present; RHS color chart value) | N198A | 189A |
| | leaf blade: color | blue green (Citation, Esquire, Symphony) | grey green (Bishop) |
| | leaf blade: intensity of color | medium | medium |
| | leaf blade: anthocyanin coloration | absent (Claudia, Embassy) | absent (Claudia, Embassy) |
| | leaf blade: undulation of margin | weak (Beaufort, Early Pack, Laser, Paladin) | strong (Aikido, Marathon, Samurai) |
| | leaf blade: dentation of margin | weak (Galaxy) | weak (Galaxy) |
| | outer leaves: leaf shape | elliptic | elliptic |
| | outer leaves: leaf base | blunt | blunt |
| | outer leaves: leaf apex | blunt | blunt |
| | outer leaves: leaf margins | slightly wavy | very wavy |
| | outer leaves: leaf veins | intermediate | thin |
| | outer leaves: midrib | slightly raised | not raised |
| | leaf blade: blistering | absent or very weak (Buccaneer, Colibri) | absent or very weak (Buccaneer, Colibri) |
| | outer leaves: attitude (leaf angle from ground) | semi-erect (35-55 degrees) | semi-erect (35-55 degrees) |
| | leaf: attitude (at beginning of head formation) | semi-erect (Arcadia, Asti, Civet, Claudia) | semi-erect |
| | outer leaves: torsion of leaf tip | none | weak |
| | outer leaves: profile of upper side of leaf | concave | convex |
| F | Head | | |
| | length of branching at base (excluding stem) | short (Brigadeer, Buccaneer Emperor) | medium (Capitol, Green Duke, Perseus) |
| | diameter at widest point (at market maturity) | 11.4 cm | 13.7 cm |
| | depth (at market maturity) | 10.4 cm | 10.9 cm |
| | weight, market trimmed (at market maturity) | 164.3 gm | 182.7 gm |
| | color | light green; grey-green (Brigadeer, Galaxy) | grey-green (Brigadeer, Galaxy) |
| | intensity of color | medium | medium |
| | RHS color chart value for head color | 189A/144A | N189B |
| | anthocyanin coloration | absent (Early White Sprouting) | absent (Early White Sprouting) |
| | shape (at market maturity) | circular (Esquire) | transverse elliptic (Buccaneer, Futura) |

TABLE 3-continued

Physiological and Morphological Characteristics of Line BRM 53-3934 SI

| | Characteristic | BMR53-3934SI | Sibsey |
|---|---|---|---|
| | dome shape (at market maturity) | domed | domed |
| | size (at market maturity) for US Exhibit C only choice | very small (Early Purple Sprouting) | small (Orbit, Scorpio) |
| | compactness/firmness (at market maturity) | long pedicels/loose (Caravel) | medium (Late Corona) |
| | surface knobbling (at market maturity) | medium (Southern Comet) | fine (Apollo, Brigadeer) |
| | texture | fine (Auriga, Bishop, Green Top); coarse (Citation) | fine (Auriga, Bishop, Green Top) |
| | bead size (at market maturity) | small/medium/large | small |
| | flower buds (at market maturity) | uneven in size (cateye) | even in size |
| | anthocyanin coloration of leaf axils (at market maturity) | absent | absent |
| | anthocyanin coloration of leaf veins (at market maturity) | absent | absent |
| | anthocyanin coloration of leaf blade (at market maturity) | absent | absent |
| | anthocyanin coloration of entire plant (at market maturity) | absent | absent |
| | anthocyanin coloration of leaf petiole (at market maturity) | absent (Claudia, Embassy) | absent (Claudia, Embassy) |
| | color of head leaves (at market maturity) | green | green |
| | RHS color chart value for the color of head leaves | N189B | 189A |
| | bracts | present (Ramoso Calabrese) | absent (Gem, Orion) |
| | secondary heads (at market maturity) | basal, present** (Marathon, Tribute, Late Purple Sprouting) | combination |
| | prominence of secondary heads (at market maturity) | intermediate (Citation) | intermediate (Citation) |
| | number of secondary heads (at market maturity) | 3 | 4 |
| G | Flower | | |
| | Color choice for UPOV TG only | yellow (Brigadeer, Orion) | yellow** (Brigadeer, Orion) |
| | intensity of yellow color | dark (Gem, Orion) | dark (Gem, Orion) |
| | color | 4A | 4A |
| | stalk color | green | green |
| | RHS color chart value for flower stalk color | 138B | 138B |
| | male sterility | absent (Marathon) | present (Chevalier, Montop) |

*These are typical values. Values may vary due to environment. Other values that are substantially equivalent are also within the scope of the invention.

The MSB content of hybrid RX 05991199 relative to the hybrid "Heritage" was the subject of an objective analysis. The results of the analysis are presented below.

TABLE 4

Analysis of MSB Content of RX 05991199

| Varieties | Least-Squares Means for MSB (micromoles/gm/FW) |
|---|---|
| RX 05991199 | 3.5833927 |
| Heritage | 1.6311887 |

A head-to-head analysis was also made of glucoraphanin (MSB) content of RX 05991199 relative to the hybrid Ironman in multiple locations and plantings. The results are presented below.

TABLE 5

Analysis of Glucoraphanin Content of RX 05991199 Relative to Hybrid calculated in µmol per gDW

| Variety | Country | SubRegion | Planting | Glucoiberin | Glucoraphanin |
|---|---|---|---|---|---|
| Ironman | Italy | South | A | 2.1 | 3.9 |
| RX 05991199 | Italy | South | A | 5.0 | 20.0 |
| RX 05991199 | Italy | South | A | 1.5 | 6.7 |
| Ironman | Spain | South | B | 2.1 | 3.1 |
| RX 05991199 | Spain | South | B | 3.5 | 13.4 |
| Ironman | Italy | South | C | 3.2 | 9.2 |
| Ironman | Italy | South | C | 3.6 | 9.1 |
| Ironman | Italy | South | C | 3.4 | 10.3 |
| Ironman | Italy | South | C | 3.3 | 10.8 |
| RX 05991199 | Italy | South | C | 4.7 | 20.7 |
| RX 05991199 | Italy | South | C | 5.4 | 22.3 |
| RX 05991199 | Italy | South | C | 5.5 | 26.0 |
| RX 05991199 | Italy | South | C | 4.7 | 22.9 |
| Ironman | Spain | South | D | 1.9 | 5.5 |
| Ironman | Spain | South | D | 2.8 | 9.6 |
| Ironman | Spain | South | D | 2.4 | 5.9 |
| RX 05991199 | Spain | South | D | 5.1 | 21.7 |
| RX 05991199 | Spain | South | D | 5.5 | 24.8 |
| RX 05991199 | Spain | South | D | 5.1 | 25.7 |
| Ironman | UK | North | A | 2.5 | 9.8 |
| Ironman | UK | North | A | 3.1 | 12.8 |
| RX 05991199 | UK | North | A | 3.8 | 21.3 |
| RX 05991199 | UK | North | A | 3.4 | 24.4 |
| Ironman | UK | North | B | 0.9 | 7.1 |
| Ironman | UK | North | B | 1.9 | 12.1 |
| RX 05991199 | UK | North | B | 2.4 | 11.9 |
| RX 05991199 | UK | North | B | 3.0 | 16.0 |
| Ironman | UK | North | C | 1.8 | 5.8 |
| Ironman | UK | North | C | 1.9 | 5.8 |
| RX 05991199 | UK | North | C | 3.1 | 14.1 |
| RX 05991199 | UK | North | C | 3.3 | 15.1 |
| Ironman | UK | North | D | 1.1 | 6.2 |
| Ironman | UK | North | D | 0.9 | 6.2 |
| RX 05991199 | UK | North | D | 3.2 | 17.2 |
| RX 05991199 | UK | North | D | 3.1 | 16.6 |
| ironman | Italy | South | F | 0.9 | 5.1 |
| ironman | Italy | South | F | 1.0 | 5.3 |
| RX 05991199 | Italy | South | F | 3.8 | 24.5 |
| RX 05991199 | Italy | South | F | 3.6 | 25.1 |
| ironman | Italy | South | A | 0.9 | 4.3 |
| ironman | Italy | South | A | 1.0 | 5.1 |
| RX 05991199 | Italy | South | A | 4.6 | 23.5 |
| RX 05991199 | Italy | South | A | 4.0 | 22.4 |
| ironman | Spain | South | B | 1.5 | 6.0 |
| ironman | Spain | South | B | 2.4 | 11.2 |
| RX 05991199 | Spain | South | B | 4.0 | 20.7 |
| RX 05991199 | Spain | South | B | 4.4 | 22.1 |
| ironman | Spain | South | C | 1.9 | 8.3 |
| ironman | Spain | South | C | 1.7 | 8.8 |
| RX 05991199 | Spain | South | C | 4.1 | 24.3 |
| RX 05991199 | Spain | South | C | 4.3 | 22.4 |
| Ironman | Spain | South | D | 1.2 | 5.5 |
| Ironman | Spain | South | D | 0.9 | 4.9 |
| RX 05991199 | Spain | South | D | 3.5 | 19.0 |
| RX 05991199 | Spain | South | D | 2.8 | 17.5 |
| Ironman | Italy | South | E | 0.9 | 7.6 |
| Ironman | Italy | South | E | 0.8 | 6.7 |
| RX 05991199 | Italy | South | E | 3.0 | 24.4 |
| RX 05991199 | Italy | South | E | 1.8 | 23.3 |
| Ironman | Spain | South | F | 0.8 | 5.0 |
| Ironman | Spain | South | F | 0.6 | 3.8 |
| RX 05991199 | Spain | South | F | 2.9 | 17.1 |
| RX 05991199 | Spain | South | F | 3.0 | 19.3 |
| Ironman | Spain | South | G | 1.0 | 6.3 |
| Ironman | Spain | South | G | 0.9 | 6.2 |
| RX 05991199 | Spain | South | G | 3.4 | 20.8 |
| RX 05991199 | Spain | South | G | 3.0 | 19.9 |
| Ironman | Spain | South | H | 2.5 | 14.7 |
| Ironman | Spain | South | H | 2.3 | 14.1 |
| RX 05991199 | Spain | South | H | 3.6 | 21.9 |
| RX 05991199 | Spain | South | H | 4.0 | 23.0 |
| Ironman | UK | North | B | 0.9 | 6.2 |
| Ironman | UK | North | B | 1.0 | 6.1 |
| RX 05991199 | UK | North | B | 4.2 | 20.9 |

TABLE 5-continued

Analysis of Glucoraphanin Content of RX 05991199 Relative to Hybrid calculated in μmol per gDW

| Variety | Country | SubRegion | Planting | Glucoiberin | Glucoraphanin |
|---|---|---|---|---|---|
| RX 05991199 | UK | North | B | 3.6 | 18.6 |
| Ironman | UK | North | C | 2.1 | 6.3 |
| Ironman | UK | North | C | 1.9 | 6.4 |
| RX 05991199 | UK | North | C | 4.7 | 15.1 |
| RX 05991199 | UK | North | C | 4.4 | 15.5 |
| Ironman | UK | North | D | 1.7 | 11.3 |
| Ironman | UK | North | D | 1.1 | 6.3 |
| RX 05991199 | UK | North | D | 4.1 | 22.0 |
| RX 05991199 | UK | North | D | 2.7 | 14.6 |
| Ironman | UK | North | E | 2.1 | 11.9 |
| RX 05991199 | UK | North | E | 5.3 | 24.2 |
| Ironman | UK | North | F | 1.2 | 8.0 |
| Ironman | UK | North | F | 1.5 | 8.7 |
| RX 05991199 | UK | North | F | 4.2 | 19.9 |
| RX 05991199 | UK | North | F | 4.5 | 21.9 |
| Ironman | UK | North | G | 1.0 | 6.1 |
| Ironman | UK | North | G | 1.0 | 6.7 |
| RX 05991199 | UK | North | G | 2.7 | 16.8 |
| RX 05991199 | UK | North | G | 2.8 | 17.7 |
| Ironman | UK | North | H | 1.0 | 6.7 |
| Ironman | UK | North | H | 0.8 | 5.8 |
| RX 05991199 | UK | North | H | 3.4 | 19.2 |
| RX 05991199 | UK | North | H | 3.9 | 23.1 |
| Ironman | Spain | South | A | 0.6 | 4.0 |
| Ironman | Spain | South | A | 0.9 | 4.2 |
| Ironman | Spain | South | A | 0.8 | 3.7 |
| RX 05991199 | Spain | South | A | 2.6 | 13.3 |
| RX 05991199 | Spain | South | A | 2.7 | 14.1 |
| RX 05991199 | Spain | South | A | 2.8 | 13.4 |
| Ironman | Italy | South | B | 1.4 | 7.3 |
| Ironman | Italy | South | B | 1.2 | 8.2 |
| RX 05991199 | Italy | South | B | 4.9 | 26.6 |
| RX 05991199 | Italy | South | B | 3.5 | 18.7 |
| Ironman | Spain | South | C | 1.1 | 5.9 |
| Ironman | Spain | South | C | 1.0 | 4.8 |
| Ironman | Spain | South | C | 1.0 | 5.5 |
| RX 05991199 | Spain | South | C | 3.3 | 16.0 |
| RX 05991199 | Spain | South | C | 2.7 | 13.0 |
| RX 05991199 | Spain | South | C | 2.9 | 11.7 |
| Ironman | Italy | South | D | 1.1 | 5.9 |
| Ironman | Italy | South | D | 1.1 | 5.3 |
| RX 05991199 | Italy | South | D | 2.9 | 16.0 |
| RX 05991199 | Italy | South | D | 3.9 | 21.4 |
| Ironman | Spain | South | E | 0.9 | 4.3 |
| Ironman | Spain | South | E | 1.0 | 3.9 |
| Ironman | Spain | South | E | 1.1 | 4.8 |
| RX 05991199 | Spain | South | E | 3.6 | 21.2 |
| RX 05991199 | Spain | South | E | 2.2 | 16.5 |
| RX 05991199 | Spain | South | E | 2.5 | 15.5 |
| Ironman | Spain | South | F | 1.1 | 4.6 |
| Ironman | Spain | South | F | 0.8 | 4.4 |
| Ironman | Spain | South | F | 1.0 | 4.5 |
| RX 05991199 | Spain | South | F | 1.5 | 9.7 |
| RX 05991199 | Spain | South | F | 2.3 | 15.4 |
| RX 05991199 | Spain | South | F | 2.4 | 15.3 |
| Ironman | Spain | South | G | 1.2 | 4.4 |
| Ironman | Spain | South | G | 1.4 | 5.6 |
| Ironman | Spain | South | G | 1.0 | 3.4 |
| RX 05991199 | Spain | South | G | 2.9 | 16.7 |
| RX 05991199 | Spain | South | G | 2.8 | 18.7 |
| RX 05991199 | Spain | South | G | 3.0 | 15.9 |
| Ironman | UK | North | L | 0.7 | 8.2 |
| Ironman | UK | North | L | 0.8 | 9.8 |
| Ironman | UK | North | L | 0.8 | 10.3 |
| RX 05991199 | UK | North | L | 1.6 | 15.0 |
| RX 05991199 | UK | North | L | 1.9 | 17.1 |
| RX 05991199 | UK | North | L | 1.9 | 18.1 |
| Ironman | UK | North | M | 0.2 | 4.9 |
| Ironman | UK | North | M | 0.3 | 4.5 |
| Ironman | UK | North | M | 0.3 | 5.2 |
| RX 05991199 | UK | North | M | 1.1 | 8.5 |
| RX 05991199 | UK | North | M | 1.6 | 9.8 |
| RX 05991199 | UK | North | M | 1.3 | 10.0 |

Example 4

Use of Genetic Markers to Identify and Track Reduced Introgressions

Genetic marker assays were developed to genotype for Myb28 and ELONG alleles. The assays thus permit identification of a reduced introgression in accordance with the invention as well as marker assisted introduction of the reduced introgression into any other genotype.

A. Markers for Detection of ELONG

Figure 4:
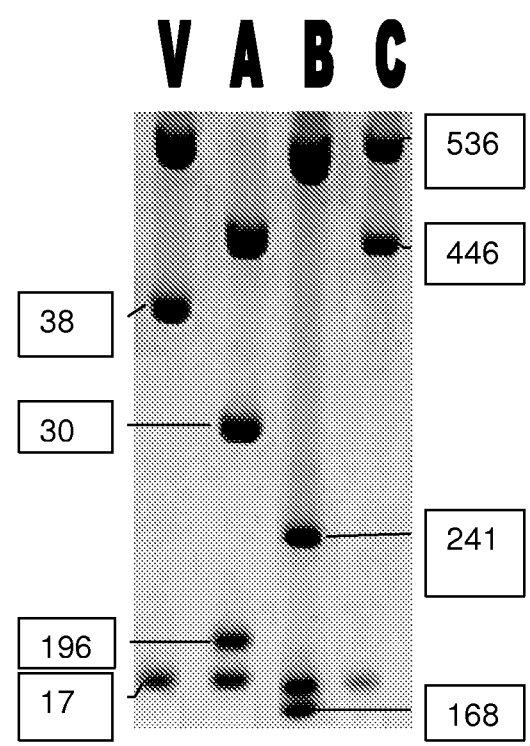
FIG. 4 shows assay results for different ELONG alleles with the QTL1-BoGLS-ELONG marker. The V allele is the *B. villosa* allele associated with Myb28, which results in high 3-MSP/4-MSB ratio and high total glucosinolates. The A, B and C alleles are examples of alleles found in broccoli without a *B. villosa* ELONG allele.

A marker designated QTL1-BoGLS-ELONG was developed and permits detection of the presence or absence of a *B. villosa* ELONG allele. This marker can be detected using the primer pair AF399834F2: 5'-cggattttcaaattttctcg-3' (SEQ ID NO:1) and AF399834R2: 5'-atttcgcatgaccactaggc-3' (SEQ ID NO:2). To detect the marker, plates were loaded with 20 ng DNA template (sample) in a 2 μL volume. 3 μL master mix (0.437 μL water, 2.5 μL Q PCR (ROX) mix, 0.063 μL assay mix) was added to each well for a final volume of 5 μL. PCR conditions were as follows: 95° C. for 15 min then 40 cycles of 95° C. for 15 sec, 60° ° C. for 1 min. FIG. 4 shows results of an assay for different ELONG alleles using the marker. The V allele is indicative of the *B. villosa* ELONG allele, while A, B and C alleles are examples of alleles found in broccoli without a *B. villosa* ELONG allele.

B. Marker for the Detection of Myb28

The identification of genetic polymorphisms in Myb28 alleles and their use as genetic markers is described in U.S. Provisional Appln. Ser. No. 61/700,731, filed concurrently herewith, the disclosure of which is incorporated herein by reference in its entirety. Specifically, sequence alignments were described therein between *B. oleracea* alleles and the corresponding Myb28 sequences to identify polymorphisms that can be used for marker based selection for a Myb28 allele of choice. The results are shown in FIG. 5, which is an alignment between a consensus sequence of the Myb28 locus from *B. villosa* contained in broccoli variety FT69, and a consensus sequence of the corresponding locus from broccoli without increased level of glucosinolate, e.g. *B. oleracea*, (Oleracea). Shown are 26 polymorphisms (e.g. single feature polymorphisms (SFPs)—of which there are 16 SNPs and 10 indels) detected in a sequence with a total length of 2202 bp. Any of these or other identified polymorphisms may be used as genetic markers for the presence or absence of a desired Myb28, including from *B. oleracea* or *B. villosa*.

A TaqMan assay (NBOLI009111370) was designed based on one of the sequence polymorphisms identified, as follows:

```
NBOLI009111370 sequence (SEQ ID NO: 3):
GACCACCTAAAGACAAGAATAGTGAAAGAGATAAGATGGAAGACCAAAGT

TAATCAAATTTATTTTGAAGCTTTT[C/T]TATGGAATAGAGACTAAAAT

GATGTGTGCTATTGCAATTTTTAGTCACATATTGCTAATCAAACACATAT

TTTGCATCAGAGAATTGTCAAATACATGAAAAAAATAAAGAATAATTTTT

Forward primer (SEQ ID NO: 4):
GTGAAAGAGATAAGATGGAAGACCAAAGT

Reverse primer (SEQ ID NO: 5):
GTGACTAAAAATTGCAATAGCACACATCA
```

```
Vic probe (SEQ ID NO: 6):
CTATTCCATAGAAAAGC

Fam probe (SEQ ID NO: 7):
CTATTCCATAAAAAGC
```

The assay was carried out using standard procedures as follows: Load plates with 20 ng DNA template in 5 μL volume. Add 10 μL master mix (2 parts each of 1×PCR mix, 0.437 μL water, 2.5 μL Q PCR (ROX) mix, 0.063 μL assay mix, 2 μL primers at 5 ng/μL) to each well for a final volume of 15 μL.

PCR conditions are as follows: 50° C. for 2 min followed by 95° C. for 2 min then 40 cycles of 95° C. for 15 sec, 60° ° C. for 1 min.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method for producing a hybrid *Brassica oleracea* plant with elevated glucosinolate content comprising crossing a first *Brassica oleracea* parent plant with a second *Brassica oleracea* plant of a different genotype, wherein the first parent plant comprises a Myb28 allele from *Brassica villosa* that lacks an ELONG allele from *Brassica villosa* genetically linked to said Myb28 allele, wherein the Myb28 allele confers elevated glucosinolates relative to a plant lacking the Myb28 allele, and wherein a sample of seed comprising said Myb28 allele is deposited under ATCC Accession No. PTA-13165.

2. The method of claim 1, further comprising producing a plurality of hybrid *Brassica oleracea* plants comprising crossing the first *Brassica oleracea* parent plant with a plurality of second *Brassica oleracea* plants of different genotypes.

3. A method of producing a *Brassica oleracea* plant with a desired elevated glucosinolate content comprising introgressing into the plant a chromosomal segment comprising a Myb28 allele from *Brassica villosa* and lacking an ELONG allele from *Brassica villosa* genetically linked to said Myb28 allele, wherein segment confers a desired glucosinolate content relative to a plant lacking the segment, wherein a sample of seed comprising the chromosomal segment is deposited under ATCC Accession No PTA-13165.

* * * * *

```
                               SEQUENCE LISTING

Sequence total quantity: 9
SEQ ID NO: 1            moltype = DNA  length = 20
FEATURE                 Location/Qualifiers
source                  1..20
                        mol_type = other DNA
                        note = Primer
                        organism = synthetic construct
SEQUENCE: 1
cggattttca aattttctcg                                                   20

SEQ ID NO: 2            moltype = DNA  length = 20
FEATURE                 Location/Qualifiers
source                  1..20
                        mol_type = other DNA
                        note = Primer
                        organism = synthetic construct
SEQUENCE: 2
atttcgcatg accactaggc                                                   20

SEQ ID NO: 3            moltype = DNA  length = 196
FEATURE                 Location/Qualifiers
source                  1..196
                        mol_type = other DNA
                        note = Taqman assay NBOLI009111370
                        organism = synthetic construct
SEQUENCE: 3
gaccacctaa agacaagaat agtgaaagag ataagatgga agaccaaagt taatcaaatt        60
tattttgaag cttttytatg gaatagagac taaaatgatg tgtgctattg caatttttag       120
tcacatattg ctaatcaaac acatattttg catcagagaa ttgtcaaata catgaaaaaa       180
ataaagaata attttt                                                      196

SEQ ID NO: 4            moltype = DNA  length = 29
FEATURE                 Location/Qualifiers
source                  1..29
                        mol_type = other DNA
                        note = Forward primer
                        organism = synthetic construct
SEQUENCE: 4
gtgaaagaga taagatggaa gaccaaagt                                         29

SEQ ID NO: 5            moltype = DNA  length = 29
FEATURE                 Location/Qualifiers
source                  1..29
                        mol_type = other DNA
                        note = Reverse primer
                        organism = synthetic construct
SEQUENCE: 5
gtgactaaaa attgcaatag cacacatca                                         29

SEQ ID NO: 6            moltype = DNA  length = 17
FEATURE                 Location/Qualifiers
source                  1..17
                        mol_type = other DNA
                        note = Vic probe
                        organism = synthetic construct
SEQUENCE: 6
ctattccata gaaaagc                                                      17
```

```
SEQ ID NO: 7             moltype = DNA   length = 17
FEATURE                  Location/Qualifiers
source                   1..17
                         mol_type = other DNA
                         note = Fam probe
                         organism = synthetic construct
SEQUENCE: 7
ctattccata aaaaagc                                                        17

SEQ ID NO: 8             moltype = DNA   length = 2165
FEATURE                  Location/Qualifiers
source                   1..2165
                         mol_type = unassigned DNA
                         note = Brassica villosa FT69
                         organism = Brassica villosa
SEQUENCE: 8
gaaaatcaca gttcacgcct cttactccat gagcttctct attctcatcc tagtgttata          60
atcttgcaaa cacatataga aagcaagatt tggagtgtac gagaaaaaca tgaaaacacc         120
tagaagctct gtgggtaaga cccaagagcg tttctcgatt agtttcatat acagatgcat         180
cagagttctc atcaaccgat ctacttcttt cttatcttat tagaaaaaaa aatcctatc          240
aaaatttact ttcctgcaag tatatttttc tttacatttt catttctttg agtgttattt         300
gagtgaagtt atattaaaat attgttcata tatatcgaaa atgtcaagaa agccatgttg         360
tgtcggagaa gggctgaaga aaggggcatg gaccaccgag gaagataaga aactcatctc         420
ttacatccat gaacatggag aaggaggctg gcgcgacatt cctcaaaaag ctggttaata         480
tctattatat atttttttggt aaattttttaa aacatatata tttgtttggt atttgatgta       540
tgaaagtttt atattgaatg tggtgttttta ctaggattga aaaggtgtgg aaagagttgc        600
agactgcgat ggactaacta cctaaaacct gagatcaaaa gaggcgagtt tagttcagag         660
gaggaacaga ttatcatcat gctccatgct gctcgtggca acaagtacgt ttattttaga         720
ccaaaaaaaa acaagtacgt ttattttaaa caaaaaggac gattatatat ttttgtgtgt        780
atggatcctc cagtgatcat cattctagtt ttctccttctt ttttttatac cgcaaacaaa       840
tttcattagt aaaaaaaatt aaaattccaa agtcaatatt caaaaacaca gtgttatata        900
atcctatata tgtcatatat taaaaaagta tattaaaaaa gtacaacatg agaaatgaat        960
ttaagtatgc ttctaaagcg aagttttact tcccaaaaaa ttattcttta ttttttttcat     1020
gtatttgaca attctctgat gcaaaatatg tgtttgatta gcaatatgtg actaaaaatt       1080
gcaatagcac acatcatttt agtctctatt ccatagaaaa gcttcaaaat aaatttgatt       1140
aactttggtc ttccatctta tctctttcac tattcttgtc tttaggtggt cggtcatagc       1200
kagacattta cctagaagaa cmgacaatga gatcaagaay tactggaaca cacatctcaa       1260
gaaacgtttg atcgaacagg gtactgatcc cgtgactcac aagccactag cttctaatac       1320
aaaccctact gtacctgaga atttgcattc cctagatgca tctagttccg acaagcaata       1380
ctcccggtca agctcaatgc cttccatgtc ttgtactcct tcctccggtt tcaacacggt      1440
tttcgagaat accagcaaag atgggacacc agttcgtgag gacgattcct tgagtcgcaa      1500
gaaacgtttg aagaaatcaa gttctacatc aaggcttttg aacaaagttg cggctaaggc      1560
cacttccatg aaaaaaagctt tgtctgcttc catggaaggt agcttgaatg ctaatataag      1620
cttttccaat ggctactctg agcagattct caatgaagat gatagttcta atgcatccct      1680
cataaacact ctcgccgagt tcgatccctt cctccaaaca acgttttacc ctgagaatga      1740
gatgaatact acttctgatc tcggtataga tcaggactaa ttctcacatt ttctcgaaaa      1800
tttcggcaac cataatgagg agcactacat gaatcataac tatggtcatg gtcttcttat      1860
gtcctatgtg tcccaagaag tctcatcaac tagcgttgat gatcaagaca atactaatga      1920
gggttggtca aattatcttc ttgaccatgc tgattttata catgacatgg attctgattc      1980
cctcggaaag catctcatat gaatcttcgt gcctaagcag aaaggtttca aacttgtcag      2040
aacaagaagt tatgtatgta ttctattata tggattgttt agtatatgtc caagatcatg      2100
gttgttagtc ccaagtttag ggtttgtata atatacaata agggacgtta tcttataaaa      2160
cgagg                                                                  2165

SEQ ID NO: 9             moltype = DNA   length = 2186
FEATURE                  Location/Qualifiers
source                   1..2186
                         mol_type = unassigned DNA
                         organism = Brassica oleracea
SEQUENCE: 9
gaaaatcaca gttcacgcct cttactccat gagcttctct attctcatcc tagtgttata          60
atcttgcaaa cacatataga aagcaaggtt tggagtgtac gagaaaaaca tgaaaacacc         120
tagaagctct gtgggtgaga cccaagagcg tttctcgatt agtttcatat acagatgcat         180
cagagttctc atcaaccgat ctacttcttt cttatcttat tagaagaaaa aatcctatc          240
aaaatttact ttcctgcaag tatatttttc tttacatttt catttctttg agtgttattt         300
gagtgaagtt atattaaaat attgtaatag agttcatata tatcgaaaat gtcaagaaag         360
ccatgttgtg tcggagaagg gctgaagaaa ggggcatgga ccaccgagga agataagaaa         420
ctcatctctt acatccatga acatggagaa ggaggctggc gcgacattcc tcaaaaagct         480
ggttaatatc tattatatat tttttggtaa attttttaaa catatatatg tttgtttggt         540
atttgatgta tgaaagtttt atgttgaata tggtgtttta ctaggrttga aaaggtgtgg         600
aaagagttgt agactgcgat ggactaacta cctaaaacct gagatcaaaa gaggcgagtt         660
tagttcagag gaggaacaga ttatcatcat gctccatgct gctcgtggca acaagtacgt         720
ttattttaga ccaaaaaaaa acaagtacgt ttattttaaa caaaaaggac gattatatat         780
ttttatgtgt gtatggatcc tccagtgatc atcattctag ttttctcttt ttttttatac         840
cgcaaacaaa tttcattagt aaaaaaatta aaattccaaa gtcaatattc aaaaacacag         900
tgttatatat ataatcctat atatgtcata tattaaaaaa gtacaacatg agaaatgaat         960
ttaagtatgc ttctaaagcg aagttttact tcccgaaaaa ttattcttta ttttttttcat      1020
gtatttgaca attctctgat gcaaaatatg tgtttgatta gcaatatgtg actaaaaatt       1080
```

```
gcaatagcac acatcatttt agtctctatt ccataaaaaa gcttcaaaat aaatttgatt 1140
aactttggtc ttccatctta tctctttcac tattcttgtc tttaggtggt cggtcatagc 1200
kagacattta cctagaagaa cmgacaatga gatcaagaac tactggaaca cacatctcaa 1260
gaaacgtttg atcgaacagg gtactgatcc cgtgactcac aagccactag cttctaatac 1320
aaaccctact gtacctgaga atttgcattc cctagatgca tctagtaatt ccgacaagca 1380
atactcccgg tcaagctcaa tgccttccat gtcttgtact ccttcctccg gtttcaacac 1440
ggttttcgag aataccagca aagatgggac accagttcgt gaggacgatt ccttgagtcg 1500
caagaaacgt tttaagaaat caagttctac atcaaggctt ttgaacaaag ttgcggctaa 1560
ggccacttcc atgaaagaag ctttgtctgc ttccatggaa ggtagtttga atgctaatac 1620
aagcttttcc aatggctact ctgagcagat tctcaatgaa gatgatagtt ctaatgcatc 1680
cctcataaac actctcgccg agttcgatcc cttcctccaa acaacgtttt accctgagaa 1740
tgagatgaat actacttctg atctcggtat agatcaggac tacttctcac attttctcga 1800
aaatttcggc agagatgatg accacaatga ggagcactac atgaatcata actatggtca 1860
tgatcttctt atgtccgatg tgtcccaaga agtctcatca actagcgttg atgatcaaga 1920
caatactaat gagggttggt caaattatct tcttgaccat gctgatttta tacatgacat 1980
ggattctgat tccctcggaa agcatctcat atgaatcttc gtgcccaagc agaaaggttt 2040
caaacttttg aaacttgtca gaacaagaag ttatgtatgt attctattat atggattgtt 2100
tagtatatgt ccaagatcat ggttgttagt cccaagttta gggtttgtat aatatacaat 2160
aagggacgtt atcttataaa acgagg                                    2186
```